United States Patent [19]

Matsueda et al.

[11] Patent Number: 4,548,926

[45] Date of Patent: Oct. 22, 1985

[54] HYPOTENSIVE PEPTIDES AND THEIR USE

[75] Inventors: Rei Matsueda; Yuichiro Yabe; Mitsuo Yamazaki, all of Hiromachi; Tatsuo Kokubu; Kunio Hiwada, both of Onsen, all of Japan

[73] Assignee: Sankyo Company Limited, Tokyo, Japan

[21] Appl. No.: 618,127

[22] Filed: Jun. 7, 1984

[30] Foreign Application Priority Data

Jun. 9, 1983 [JP] Japan ................................. 58-103230

[51] Int. Cl.[4] ..................... A61K 37/00; C07C 103/52
[52] U.S. Cl. ........................................ 514/19; 514/18; 260/112.5 R
[58] Field of Search .................. 424/177; 260/112.5 R

[56] References Cited
PUBLICATIONS

Chem. Abstr., vol. 94, (1981) 79045r.
Chem. Abstr., vol. 93, (1980) 239952u; 205010v; 47210d.
Chem. Abstr., vol. 96, (1982) 143321y.
Chem. Abstr., vol. 97, (1982) 39405p.
Chem. Abstr., vol. 79, (1973) 66807f.
Chem. Abstr., vol. 88, (1978) 153006y.
Chem. Abstr., vol. 100, (1984) 151619t.
Chem. Abstr., vol. 99, (1983) 118331f.
Chem. Abstr., vol. 96, 195641x.
Chem. Abstr., vol. 68, (1968) 13399r.
Chem. Abstr., vol. 73, (1970) 77594m.

Primary Examiner—Delbert R. Phillips
Attorney, Agent, or Firm—Frishauf, Holtz, Goodman & Woodward

[57] ABSTRACT

Oligopeptides of formula (I)

$$R^1CO-NH-\underset{(S)}{CH}(CH_2\text{-imidazole})-CONH-\underset{(S)}{CH}(\text{But})-X \quad (I)$$

(wherein $R^1CO-$ is an acyl group. But is an isobutyl or sec-butyl group and X is a variety of organic groups) and salts and esters thereof have valuable renin inhibitory activity.

18 Claims, No Drawings ly 4,548,926

HYPOTENSIVE PEPTIDES AND THEIR USE

BACKGROUND TO THE INVENTION

The present invention relates to a series of new hypotensive peptides which are of particular value in the treatment of hypertension induced by failures in the renin-angiotensin system, and to their use in such treatment.

There is considerable evidence that reduction of elevated blood pressure reduces the risks of morbidity and mortality. Elevated blood pressure (hypertension) can be caused by a variety of factors and a large number of drugs are available for the treatment of hypertension, the drug of choice being dictated in large measure by the cause of the hypertension. Angiotensin (also known as hypertensin) is a polypeptide formed by the action of renin upon a plasma protein. It causes constriction of the arterioles and can produce hypertension. Hypertension of this type can be reduced by reducing the plasma concentration of angiotensin which, in turn, can be achieved by inhibiting the activity of renin. The number of available drugs having this type of activity is very limited.

Certain peptide derivatives having this type of activity are disclosed in Japanese Patent Application Kokai No. 151166/77 and may be represented by the formula $R^aCO-X-His-NH-CH(CH_2R^b)-CHO$, in which $R^a$ and $R^b$ represent various organic groups and His represents the L-histidyl group.

Other polypeptides which have been proposed for use as renin inhibitors are the angiotensinogen fragments described by Szelke et al. [Nature, 299, 555 (1982)] and the statine derivatives described by Boger et al. [Nature, 303, 81 (1983)].

We have now discovered a series of peptide derivatives having a very marked ability to inhibit the activity of renin.

BRIEF SUMMARY OF INVENTION

This compounds of the invention are peptides having the general formula (I):

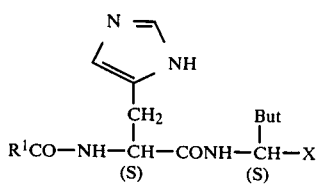

wherein:

$R^1CO-$ represents an aliphatic acyl group, an aromatic acyl group, an aromatic aliphatic acyl group, a heterocyclic acyl group or a heterocyclic aliphatic acyl group, said acyl groups being unsubstituted or having one or more substituents selected from amino groups, protected amino groups, hydroxy groups, substituted dithio groups, alkyl groups, alkoxy groups, alkoxycarbonyl groups, halogen atoms and nitro groups;

But represents a butyl group selected from the isobutyl and sec-butyl groups;

X represents
the formyl group or,
a group of formula $-CH(R^2)-Y$ (in which $R^2$ represents hydrogen, an alkyl group or a substituted alkyl group having at least one substituent selected from hydroxy groups, mercapto groups, amino groups, carbamoyl groups, formyl groups, aryl groups and heterocyclic groups and Y represents a hydroxy group, a mercapto group or a formyl group), or
a group of formula $-P(O)(R^3)-OH$ (in which $R^3$ represents a hydroxy group or a substituted alkyl or alkoxy group having at least one substituent selected from hydroxy groups, mercapto groups, amino groups, carbamoyl groups, formyl groups, aryl groups and heterocyclic groups);

and the carbon atoms marked with (S) are of the S-configuration;

provided that $R^1$ does not represent the benzyloxycarbonyl-L-phenylalanyl group or the benzyloxycarbonyl-L-propyl-L-phenylalanyl group when X represents the formyl group;

and pharmaceutically acceptable salts and esters thereof.

The invention also provides a method of treating angiotensin-induced hypertension in a mammal, which may be human or non-human, by administering to said mammal an effective amount of a renin inhibitor, wherein said renin inhibitor is selected from the group consisting of compounds of formula (I) and pharmaceutically acceptable salts and esters thereof.

DETAILED DESCRIPTION OF INVENTION

When But represents an isobutyl group, the resulting compounds of formula (Ia):

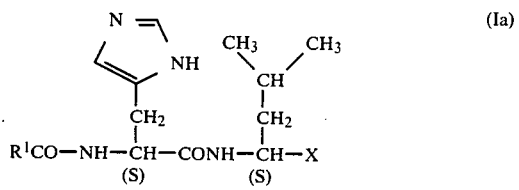

(in which $R^1$, X and S are as defined above) may be regarded as L-histidyl-L-leucine derivatives, whilst those compounds where But represents a sec-butyl group, i.e. compounds of formula (Ib):

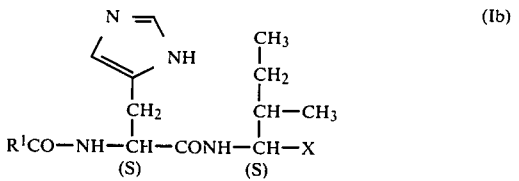

(in which $R^1$, X and S are as defined above), may be regarded as L-histidyl-L-isoleucine derivatives.

In the compounds of the invention, where $R^1CO$ represents an aliphatic acyl group, the group represented by $R^1$ is preferably a $C_1-C_6$ alkyl group, more preferably a $C_1-C_4$ alkyl group, for example a methyl, ethyl or t-butyl group.

Where $R^1CO$ represents an aromatic acyl group, the aromatic group represented by $R^1$ is preferably an optionally substituted phenyl or 1- or 2-naphthyl group.

Where $R^1CO$ represents an aromatic aliphatic acyl group, the group represented by $R^1$ is preferably an aralkyl or aralkyloxy group, in which the aryl group is preferably a phenyl or 1- or 2-naphthyl group and the alkyl group is preferably a $C_1-C_4$ alkyl group, more preferably a $C_1$ or $C_2$ alkyl group. Preferred such groups represented by $R^1$ are the benzyl, phenethyl, 2-(1-naphthyl)ethyl and 2-(2-naphthyl)ethyl groups.

Where the group represented by $R^1CO$ is a heterocyclic acyl group, the group represented by $R^1$ is a heterocyclic group, which preferably has from 4 to 8, more preferably 5 or 6, ring atoms, and which has one or more hetero-atoms selected from the group consisting of nitrogen, oxygen and sulphur, preferably nitrogen. Particularly preferred heterocyclic groups are the pyridyl groups, especially the 2- and 3-pyridyl groups: preferred heterocyclic acyl groups are, accordingly, the nicotinoyl and 2-pyridinecarbonyl groups.

Alternatively, the heterocyclic group represented by $R^1$ may be a polycyclic, and particularly an ortho-fused polycyclic, ring system, preferably having from 9 to 18 ring atoms, of which at least one and preferably 1 or 2 are hetero-atoms selected from nitrogen, oxygen and sulphur atoms, particularly nitrogen atoms. Examples of such polycyclic heterocyclic ring systems are the groups of formulae:

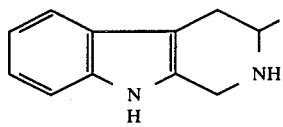

and

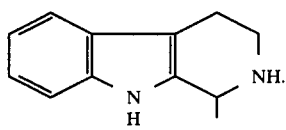

Where the group represented by $R^1CO$ is a heterocyclic aliphatic acyl group, the group represented by $R^1$ is an alkyl group (preferably having from 1 to 4 and more preferably 1 to 2 carbon atoms) having at least one and preferably one only heterocyclic substituent. The heterocyclic substituent may be any one of those referred to hereinabove, but is preferably a polycyclic heterocyclic group and most preferably a group having one of the formulae:

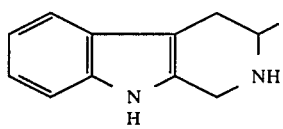

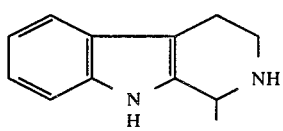

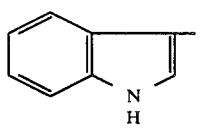

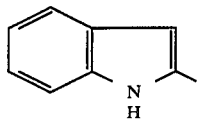

or a quinolyl or isoquinolyl group.

The above-mentioned acyl groups are all carboxylic acyl groups and may be unsubstituted or may have one or more of the aforementioned substituents. Where the substituent is a protected amino group, any protecting group commonly used in this field may be employed, particularly an alkanoyl, alkoxycarbonyl, arylthio or heterocyclicthio group, each of which may itself be substituted or unsubstituted. Where the substituent is a substituted dithio group, it is preferably a heterocyclic-substituted or phenyl-substituted dithio group; the heterocyclic ring may be any one of those described hereinabove, but is preferably a monocyclic heterocyclic ring having 5 or 6 ring atoms and is most preferably a pyridyl ring; the heterocyclic or phenyl substituent may itself be substituted, e.g. by a nitro group. Where the substituent is an alkyl group, this is preferably a $C_1$-$C_6$ and more preferably $C_1$-$C_3$ alkyl group, such as those exemplified above. Where the substituent is an alkoxy group, this is preferably a $C_1$-$C_4$ alkoxy group and, where the substituent is an alkoxycarbonyl group, the alkoxy moiety thereof is likewise preferably a $C_1$-$C_4$ alkoxy group. Where the substituent is a halogen atom, this is preferably a chlorine, fluorine or bromine atom.

Particularly preferred examples of acyl groups which may be represented by $R^1CO-$ are the acetyl, propionyl, pivaloyl, benzoyl, 2-methoxycarbonylbenzoyl, 1-naphthoyl, 2-naphthoyl, phenylacetyl, benzyloxycarbonyl, phenylalanyl, N-(benzyloxycarbonyl)phenylalanyl, alpha-(benzyloxycarbonylamino)phenylacetyl, N-(4-phenylbutyryl)phenylalanyl, 2-hydroxy-3-phenylpropionyl, N-(benzyloxycarbonyl)-tyrosyl, N-(2-nitrophenylthio)phenylalanyl, N-(3-nitro-2-pyridylthio)-phenylalanyl, 2-benzyloxycarbonylamino-3-(1-naphthoyl)propionyl, 2-benzyloxycarbonylamino-3-(2-naphthoyl)propionyl, nicotinyl, 2-pyridinecarbonyl, N-benzyloxycarbonyl-3-(3-quinolyl)-L-alanyl and N-benzyloxycarbonyl-3-(8quinolyl)-L-alanyl groups, as well as the groups having the formulae:

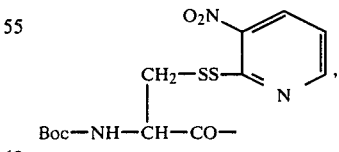

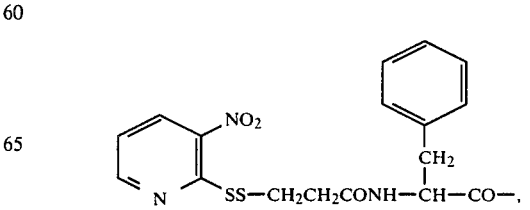

-continued

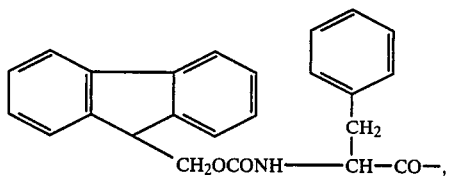

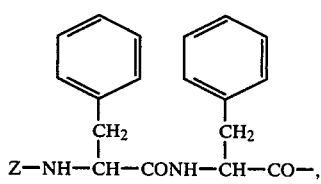

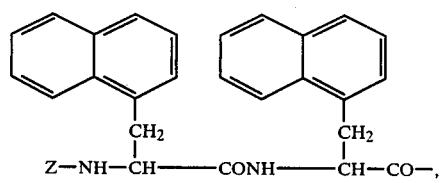

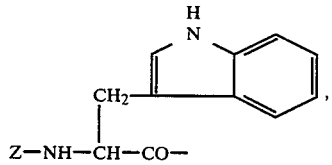

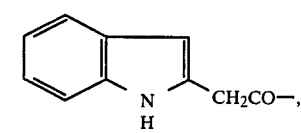

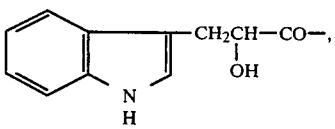

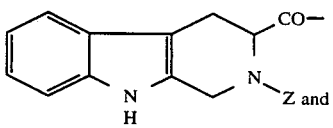

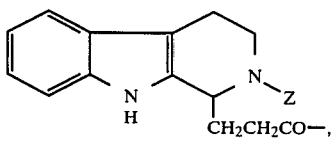

in which Boc represents the t-butoxycarbonyl group and Z represents the benzyloxycarbonyl group.

Where X represents a group of formula —CH(R-$^2$)—Y and R$^2$ represents an alkyl group, this is preferably an alkyl group having from 1 to 8 carbon atoms, for example a methyl, ethyl, propyl, isopropyl, butyl, t-butyl, sec-butyl, pentyl, isopentyl, t-pentyl, hexyl, 2ethylbutyl, heptyl, octyl or 2-ethylhexyl group. Such alkyl groups maybe unsubstituted or may have one or more substituents selected from hydroxy, mercapto, amino, carbamoyl, formyl, aryl and heterocyclic groups. Where the substituent is an aryl group, this is preferably a phenyl or 1- or 2-naphthyl group. Where the substituent is a heterocyclic group, this may be any one of the heterocyclic groups referred to hereinabove and in this case is preferably an imidazolyl group, particularly a 4-imidazolyl group.

Where X represents a group of formula —P(O)(R-$^3$)—OH, and R$^3$ represents a substituted alkyl group, examples of such groups are as given in relation to R$^2$. Where R$^3$ represents a substituted alkoxy group, the alkoxy group preferably has from 1 to 4 carbon atoms, more preferably 1 or 2 carbon atoms, and the substituents may be any of those described in relation to the substituted alkyl group represented by R$^2$; the preferred substituted alkoxy group is the 2-hydroxyethyl group.

Specific examples of groups which may be represented by X are the formyl, hydroxymethyl, formylmethyl, 2-formyl-1-hydroxyethyl, 1,2-dihydroxyethyl, 1,3-dihydroxypropyl, 2-hydroxy-1-mercaptoethyl, phosphono, hydroxo(2-hydroxyethyl)oxophosphorio and (formylmethyl)hydroxooxophosphorio groups and groups of formulae

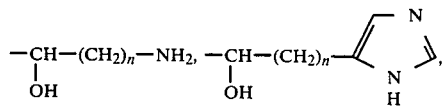

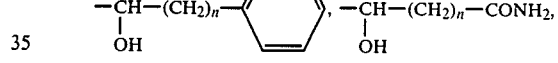

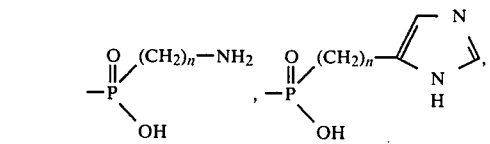

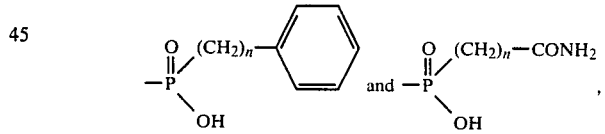

in which n represents an integer from 2 to 8.

Preferred examples of the compounds of the invention are listed below; the compounds are hereinafter identified by the numbers appended to them in this list:

1. N-(4-phenylbutyryl)-L-phenylalanyl-L-histidyl-L-leucinal, of formula

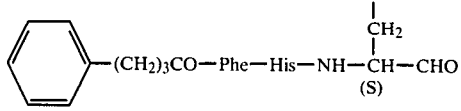

2. N-[3-(3-nitro-2-pyridyldithio)propionyl]-L-phenylalanyl-L-histidyl-L-leucinal, of formula 3. N-benzyloxycarbonyl-3-(1-naphthyl)-L-alanyl-L-histidyl-L-leucinal, of formula 4. 3(S)-(N-benzyloxycarbonyl-L-phenylalanyl-L-histidyl)amino-5-methylhexanal, of formula 5. N-benzyloxycarbonyl-L-tyrosyl-L-histidyl-L-leucinal, of formula 6. N-benzyloxycarbonyl-L-tryptophyl-L-histidyl-L-leucinal, of formula 7. N-(2-benzyloxycarbonyl-1,2,3,4-tetrahydro-β-carbolin-3-ylcarbonyl)-L-histidyl-L-leucinal, of formula 8. (3S,4S)-4-[N-benzyloxycarbonyl-3-(1-naphthyl)-L-alanyl-L-histidyl]amino-3-hydroxy-6-methylheptanal, of formula 9. 5(S)-(N-benzyloxycarbonyl-L-phenylalanyl-L-histidyl)amino-4-hydroxy-7-methyloctanal, of formula 10. N-benzyloxycarbonyl-L-phenylalanyl-L-histidyl-L-leucinol, of formula 11. N-[3-(3-nitro-2-pyridyldithio)propionyl]-L-phenylalanyl-L-histidyl-L-leucinol, of formula 12. N-t-butoxycarbonyl-S-(3-nitro-2-pyridylthio-L-cysteinyl-L-phenylalanyl-L-histidyl-L-leucinol, of formula 13. 3(S)-(N-benzyloxycarbonyl-L-phenylalanyl-L-histidyl)amino-5-methyl-1,2-hexanediol, of formula 14. N-benzyloxycarbonyl-3-(1-naphthyl)-L-alanyl-L-histidyl-L-leucinol, of formula

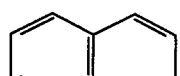 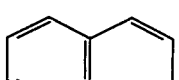
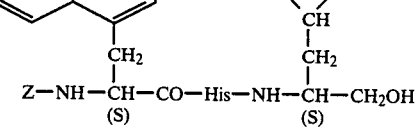 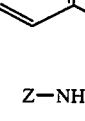 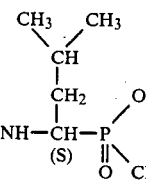

15. 4(S)-[N-benzyloxycarbonyl-3-(1-naphthyl)-L-alanyl-L-histidyl]amino-6-methyl-1,3-heptanediol, of formula 20. [1-(N-benzyloxycarbonyl-3-1'-naphthyl-L-alanyl-L-histidyl)amino-3-methylbutyl](2-hydroxyethyl)phosphinic acid, of formula

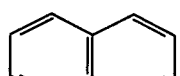 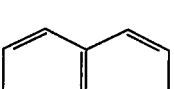
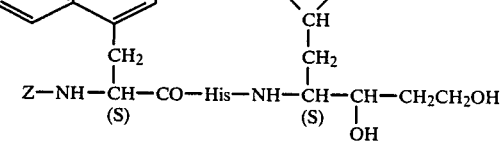  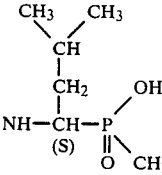

16. 5(S)-(N-benzyloxycarbonyl-L-phenylalanyl-L-histidyl)amino-7-methyl-1,4-octanediol, of formula 21. N-benzyloxycarbonyl-3-(1-naphthyl)-D-alanyl-L-histidyl-L-leucinol, of formula

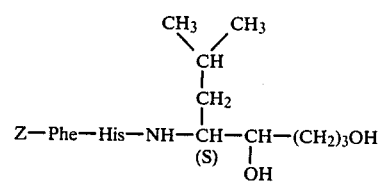

17. 1-(N-benzyloxycarbonyl-L-phenylalanyl-L-histidyl)amino-3-methylbutyl-1-phosphonic acid, of formula

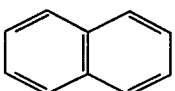 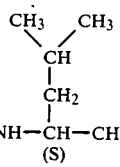

22. 3-(1-naphthyl)-L-alanyl-L-histidyl-L-leucinol dihydrobromide, of formula

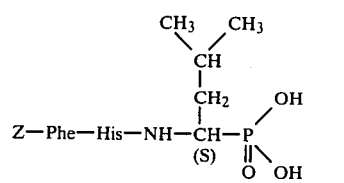

18. 2-hydroxyethyl hydrogen P-[1-(N-benzyloxycarbonyl-L-phenylalanyl-L-histidyl)amino-3-methyl-1-butyl]phosphonate, of formula

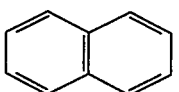 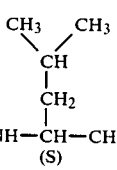

23. 3-(1-naphthyl)-D-alanyl-L-histidyl-L-leucinol dihydrobromide, of formula

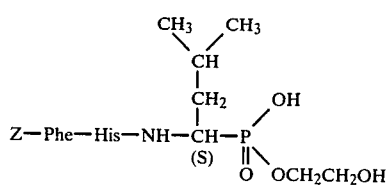

19. [1-(N-benzyloxycarbonyl-3-1'-naphthyl-L-alanyl-L-histidyl)amino-3-methylbutyl](formylmethyl)phosphonic acid, of formula

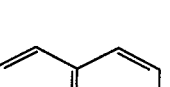 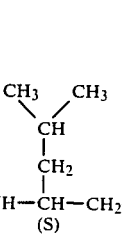

24. N-benzyloxycarbonyl-3-(1-naphthyl)-L-alanyl-L-histidyl-L-isoleucinol, of formula

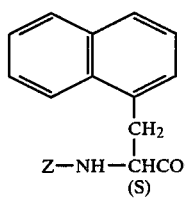                    (24)

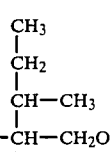

Z—NH—CHCO—His—NH—CH—CH₂OH
      (S)                (S)

25. (3S,4S)-4-[N-benzyloxycarbonyl-3-(1-naphthyl)-L-alanyl-L-histidyl]amino-3-hydroxy-6-methylheptanamide, of formula

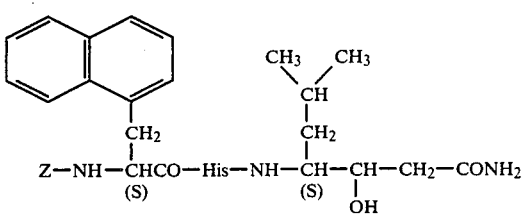                    (25)

Z—NH—CHCO—His—NH—CH—CH—CH₂—CONH₂
      (S)                (S)  |
                              OH

In the above formulae, the abbreviations Phe, His, Tyr and Trp represent the L-phenylalanyl, L-histidyl, L-tyrosyl and L-tryptophyl groups, respectively; the abbreviations Boc and Z are as defined above; and carbon atoms marked with "(S)" or "(R)" mean that those carbon atoms are in the S-configuration or the R-configuration, respectively.

The compounds of the invention include pharmaceutically acceptable salts of the compounds of formula (I). Since the compounds of formula (I) contain basic nitrogen atoms and may, depending upon the nature of the group represented by X, also contain acidic groups, such salts may be acid addition salts or salts with bases. The nature of the salt is not critical, provided that it is pharmaceutically acceptable, and acids and bases which may be employed to form such salts are, of course, well known to those skilled in this art. Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases, such as dicyclohexylamine. All of these salts may be prepared by conventional means from the corresponding compound of formula (I), for example simply by reacting the appropriate acid or base with the compound of formula (I).

The compounds of the present invention also include the esters of compounds of formulae (I), (Ia) and (Ib). Examples of such esters include C₁–C₆ alkyl esters, aralkyl esters and pyridylmethyl esters. Examples of alkyl esters include the methyl, ethyl, propyl, isopropyl, butyl, isobutyl, pentyl, isopentyl, hexyl and isohexyl esters; of these, C₁–C₄ alkyl esters are preferred, particularly the ethyl, methyl, propyl, isopropyl and butyl esters. In these esters, the alkyl group may be substituted or unsubstituted. Examples of aralkyl esters include the benzyl and phenethyl esters, in which the aromatic ring may be substituted or unsubstituted. Where the alkyl or aralkyl group is substituted, the substituents may be one or more of the following: C₁–C₆ alkyl groups, e.g. methyl, ethyl, propyl or isopropyl groups; C₁–C₆ alkoxy groups, e.g. methoxy, ethoxy, propoxy or isopropoxy groups; hydroxy groups; halogen atoms, e.g. fluorine, chlorine or bromine atoms; or trifluoromethyl groups. In the case of pyridylmethyl esters, these may be the 2-, 3- or 4-pyridylmethyl esters.

The compounds of the present invention can be prepared by conventional processes.

For example, the compounds of the invention, especially alcohol products [in which the substituent X in the desired compound (I) represents a hydroxy group], thioalcohol products [in which X represents a mercapto group] or phosphonic acid products [in which X represents the group —P(O)(R³)—OH], can be prepared by any conventional process used in peptide synthesis, for example, the azide process, the active ester process, the mixed acid anhydride process, the carbodiimide process or the condensation process using an oxidation-reduction system from a carboxylic acid having the general formula (II):

R¹CO—His—OH                    (II)

wherein R¹ and His have the same meaning as above), or a reactive derivative thereof, and an amino compound having the general formula (III):

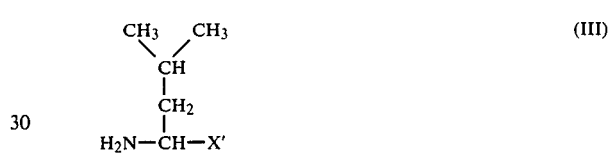                    (III)

(in which X' represents any of the groups represented by X, but preferably except a formyl group and groups containing a formyl group).

Aldehyde products in which the substituent X of the desired compound (I) is or includes a formyl group can be prepared according to the process described in Japanese Patent Application Kokai No. 151166/77 from a corresponding compound having a C-terminal aldehyde group protected, for example, with a carbonyl reagent by removing the protecting group by a conventional method to regenerate the aldehyde moiety. They can also be prepared from a corresponding alcohol product [provided that the imidazole group in the L-histidyl moiety of a compound containing a C-terminal alcohol group is protected with a protecting group such as, for example, a 2,4-dinitrophenyl group] by an oxidation reaction method such as that of Hamada et al. (Y Hamada and T. Shioiri, Chem. Pharm. Bull. 1921 (1982) in which the alcohol product is oxidized in dimethyl sulphoxide with pyridine-sulphur trioxide, which has the formula:

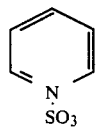

INHIBITION OF RENIN ACTIVITY

The ability of various compounds of the invention to inhibit the activity of renin was determined according to the following method.

Specifically, each test compound was dissolved in 60% v/v aqueous ethanol. Human renin activity in the presence and absence of each compound was measured using sheep angiotensinogen. The total volume of 1 ml of assay mixture contained 0.1 mole/liter phosphate buffer (pH 7.3), human renin (equivalent to 0.5 ng angiotensin I per ml per minute), sheep angiotensinogen (equivalent to 200 ng angiotensin I), the indicated concentration of the test compound, 6% ethanol and angiotensinase inhibitors (10 mmole/liter sodium ethylenediaminetetraacetate and 3.4 mmole/liter 8-hydroxyquinoline). The mixture was allowed to react for 10 minutes at 37° C., and then the reaction was stopped by placing the reaction tube in a boiling water bath for 5 minutes. The mixture was then centrifuged and the supernatant (0.05–0.1 ml) was used to assay remaining angiotensin I.

An identical experiment was carried out, as a control, except that the test compound was omitted. From the values obtained were calculated the % inhibition of renin activity achieved by each test compound. The results are shown in the following Table, in which the compounds of the invention are identified by the numbers assigned to them in the foregoing list. The values given are the mean of 3 or 4 experiments.

TABLE

| Compound No. | % Inhibition ($5 \times 10^{-5}$ mole/liter) |
| --- | --- |
| 1 | 53 |
| 2 | 70 |
| 3 | 54 |
| 10 | 58 |
| 11 | 70 |
| 14 | 71 |

As can be seen from the above Table, the compounds of the invention have a substantial inhibitory effect on the activity of human renin and are thus useful for the diagnosis and therapy of renin/angiotensin-induced hypertension in humans and other animals.

The route of administration may be oral or parenteral and the compound of the invention may be formulated accordingly, normally with a pharmaceutically acceptable carrier or diluent as, for example, a tablet, capsule, granule, powder or syrup for oral administration or as an injection or suppository for parenteral administration. The dosage will vary depending upon the age, symptoms and body weight of the patient as well as upon the desired end result, but normally we would anticipate a dose of from 0.01 mg. to 100 mg. per Kg. body weight per day, which may be administered in a single dose or in divided doses.

The invention is further illustrated by the following non-limited Examples. In the Examples, all of the values for specific rotation were measured using the sodium D line, i.e. all values are $[\alpha]_D$.

EXAMPLE 1

N-Benzyloxycarbonyl-3-(1-naphthyl)-L-alanyl-L-histidyl-L-leucinal(Compound No. 3)

(a) To a solution of 500 mg. (1 mmole) of N-benzyloxycarbonyl-3-(1-naphthyl)-L-alanyl-L-histidine hydrazide in 10 ml. of dimethylformamide was added 0.82 ml of 4.1N hydrogen chloride/dioxane. The mixture was cooled to −60° C., and then there was added 0.2 ml. of isopentyl nitrite, after which the temperature of the mixture was raised to −20° C. The disappearance of the hydrazide was confirmed, and then the temperature of the mixture was lowered to −60° C., after which it was neutralized by the addition of 0.34 g. of N-methylmorpholine, to prepare a solution of N-benzyloxycarbonyl-3-(1-naphthyl)-L-alanyl-L-histidine azide.

Separately, a solution of 337 mg. (1.1 mmole) of N-benzyloxycarbonyl-L-leucinal semicarbazone in a 25% w/v glacial acetic acid solution of hydrogen bromide was stirred at room temperature for 30 minutes, and then anhydrous diethyl ether was added to form a precipitate, which was separated by filtration. To a solution of the precipitate in 5 ml. of dimethylformamide was added 0.11 g. of N-methylmorpholine, to prepare a solution of L-leucinal semicarbazone.

To the cold azide solution previously prepared was added dropwise the semicarbazone solution prepared as described above. The mixture was stirred overnight at 4° C., and the solvent was then removed from the resulting solution by distillation under reduced pressure. To the residue was added a 5% w/v aqueous solution of sodium bicarbonate to form a colourless precipitate, which was separated by filtration and washed thoroughly with water. There were obtained 564 mg. of N-benzyloxycarbonyl-3-(1-naphthyl)-L-alanyl-L-histidyl-L-leucinal semicarbazone as an amorphous solid, melting at 192°–195° C.; $[\alpha]^{22} -21.4°$ (C=0.5, methanol).

Elemental analysis: Calculated for $C_{34}H_{39}O_5N_8 \cdot H_2O$: C, 62.09%; H, 6.28%; N, 17.04%. Found: C, 61.87%; H, 6.45%; N, 16.93%.

(b) A solution of 200 mg. of N-benzyloxycarbonyl-3-(1-naphthyl)-L-alanyl-L-histidyl-L-leucinal semicarbazone in 2 ml. of the upper layer of a 4:1:5 by volume mixture of 1-butanol, glacial acetic acid and water was subjected to partition chromatography on a Sephadex (trade mark) G-25 column (column size: 2.5 cm. inner diameter × 100.5 cm. length) and eluted with the same solvent as above. Fractions coloured with Pauli's reagent and 2,4-dinitrophenylhydrazine were collected and the solvent was removed under reduced pressure from the collected fractions. When diethyl ether was added to the residue, there were obtained 96 mg. of the desired compound as a white powdery solid, melting at 106°–108° C.; $[\alpha]^{22} -49.0°$ (C=0.5, methanol).

Elemental analysis: Calculated for $C_{33}H_{36}O_5N_5 \cdot \frac{1}{2} H_2O$: C, 66.99%; H, 6.30%; N, 11.84%. Found: C, 66.87%; H, 6.51%; N, 11.72%.

EXAMPLE 2

N-Benzyloxycarbonyl-L-tryptophyl-L-histidyl-L-leucinal(Compound No. 6)

(a) The procedure described in Example 1(a) was repeated, but using 490 mg. (1 mmole) of N-benzyloxycarbonyl-L-tryptophyl-L-histidine hydrazide. There were obtained 486 mg. of N-benzyloxycarbonyl-L-tryptophyl-L-histidyl-L-leucinal semicarbazone, melting at 123°–128° C.; $[\alpha]^{22} -8.0°$ (C=0.5, methanol).

Elemental analysis: Calculated for $C_{32}H_{38}O_5N_9 \cdot H_2O$: C, 59.43%; H, 6.23%; N, 19.49%. Found: C, 59.51%; H, 6.32%; N, 19.33%.

(b) The procedure described in Example 1(b) for partition chromatography on Sephadex G-25 was repeated, but using 150 mg. of N-benzyloxycarbonyl-L-tryptophyl-L-histidyl-L-leucinal semicarbazone. There were obtained 77 mg. of the desired compound as a white powdery solid, melting at 109°–110° C.; $[\alpha]^{22} -20.2°$ C. (C=0.5, methanol).

Elemental analysis: Calculated for $C_{31}H_{35}O_5N_6 \cdot H_2O$: C, 63.14%; H, 6.32%; N, 14.25%. Found: C, 63.49%; H, 6.16%; N, 14.01%.

EXAMPLE 3

N-Benzyloxycarbonyl-L-tyrosyl-L-histidyl-L-leucinal(Compound No. 5)

(a) The procedure described in Example 1(a) was repeated, but using 233 mg. (0.5 mmole) of N-benzyloxycarbonyl-L-tyrosyl-L-histidine hydrazide. There were obtained 221 mg. of N-benzyloxycarbonyl-L-tyrosyl-L-histidyl-L-leucinal semicarbazone, melting at 127°–137° C.; $[\alpha]^{22} -23.6°$ (C=0.5, methanol).

Elemental analysis: Calculated for $C_{30}H_{38}O_6N_8 \cdot H_2O$: C, 57.68%; H, 6.45%; N, 17.94%. Found: C, 57.51%; H, 6.63%; N, 17.73%.

(b) The procedure described in Example 1(b) for partition chromatography on Sephadex G-25 was repeated, but using 160 mg. of N-benzyloxycarbonyl-L-tyrosyl-L-histidyl-L-leucinal semicarbazone. There were obtained 87 mg. of the desired compound as a white powdery solid, melting at 105°–108° C.; $[\alpha]^{22} -26.8°$ (C=0.5, methanol).

Elemental analysis: Calculated for $C_{29}H_{35}O_6N_5 \cdot 1.5 H_2O$: C, 60.40%; H, 6.64%; N, 12.14%. Found: C, 60.64%; H, 6.52%; N, 12.32%.

EXAMPLE 4

N-[3-(3-Nitro-2-pyridyldithio)propionyl]-L-phenylalanyl-L-histidyl-L-leucinal(Compound No. 2)

(a) A solution of 181 mg. (0.3 mmole) of N-benzyloxycarbonyl-L-phenylalanyl-L-histidyl-L-leucinal semicarbazone prepared by the method of Ito et al. (Japanese Patent Application Kokai No. 151166/77) in 3 ml. of a 25% w/v glacial acetic acid solution of hydrogen bromide was stirred at room temperature for 30 minutes, after which anhydrous diethyl ether was added to form a precipitate. To a solution of the precipitate in 4 ml. of dimethylformamide were added 60 mg. of triethylamine, followed by 86 mg. (0.33 mmole) of 3-(3-nitro-2-pyridyldithio)propionic acid and 39 mg. (0.33 mmole) of 1-hydroxybenztriazole. The resulting mixture was cooled with ice and then there was added a solution of 74 mg. (0.36 mmole) of dicyclohexylcarbodiimide (DCC) in 4 ml. of methylene chloride. The mixture was cooled with ice for 1 hour and then stirred overnight at room temperature. The resulting mixture was treated by a conventional method to give a yellow powder, which was purified by silica gel column chromatography (eluent: chloroform/methanol=10:1 by volume). There were obtained 70 mg. of N-[3-(3-nitro-2-pyridyldithio)propionyl]-L-phenylalanyl-L-histidyl-L-leucinal semicarbazone.

(b) The whole of the semicarbazone prepared as described in step (a) was treated in the same way as in Example 1(b) by partition chromatography using Sephadex G-25. There were obtained 48 mg. of the desired compound as a yellow powdery solid, melting at 101°–105° C.; $[\alpha]^{22} -24.6°$ (C=0.5, methanol).

Elemental analysis: Calculated for $C_{29}H_{35}O_6N_7S_2$: C, 54.28%; H, 5.50%; N, 15.28%; S, 10.00%. Found: C, 54.43%; H, 5.32%; N, 15.01%; S, 10.05%.

EXAMPLE 5

N-(4-Phenylbutyryl)-L-phenylalanyl-L-histidyl-L-leucinal(Compound No. 1)

(a) The procedure described in Example 4(a) was repeated, but using 54 mg. (0.33 mmole) of 4-phenylbutyric acid. There were obtained 128 mg. of N-(4-phenylbutyryl)-L-phenylalanyl-L-histidyl-L-leucinal semicarbazone.

(b) The whole of the semicarbazone prepared as described in step (a) was treated in the same way as in Example 1(b) by partition chromatography using Sephadex G-25. There were obtained 42 mg. of the desired compound as a white powdery solid, melting at 98°–103° C.; $[\alpha]^{22} -6.0°$ (C=0.5, methanol).

Elemental analysis: Calculated for $C_{31}H_{39}O_4N_5$: C, 68.23%; H, 7.20%; N, 12.83%. Found: C, 68.50%; H, 7.29%; N, 12.71%.

EXAMPLE 6

3(S)-(N-Benzyloxycarbonyl-L-phenylalanyl-L-histidyl-)amino-5-methylhexanal(Compound No. 4)

(a) 1.56 g. (9.3 mmole) of 3(S)-amino-5-methylhexanoic acid hydrochloride [prepared by the method of K. Balenovic et al. (J. Chem. Soc., 1952, 3316)] were converted to the methyl ester in a conventional way with methanol-thionyl chloride. To the ester were added 14 ml. of ethyl acetate and 22 ml. of a 1N aqueous solution of sodium bicarbonate. To the mixture were added dropwise, whilst cooling with ice, 1.88 g. (1.1 mmole) of benzyloxycarbonyl chloride. The mixture was stirred for 2 hours, and then placed in a separation funnel, after which the organic layer was separated, washed with ice and dried over anhydrous sodium sulphate. The solvent was then removed by distillation under reduced pressure, and the residual syrup was purified by silica gel column chromatography (eluent: methylene chloride). There were obtained 1.52 g. of methyl 3(S)-benzyloxycarbonylamino-5-methylhexanoate as a syrup.

Nuclear magnetic resonance spectrum ($CDCl_3$) δ ppm:

0.90 (6H, doublet, J=6 Hz, —$CH_3$);
1.08–1.96 (3H, multiplet, C$\underline{H}$, C$\underline{H}_2$);
2.48 (2H, doublet, J=6 Hz, C$\underline{H}_2CO_2$);
3.60 (3H, singlet, $CO_2CH_3$);
3.83–4.40 (1H, multiplet, NHC$\underline{H}$);
5.15–5.55 (1H, broad, N$\underline{H}$);
7.29 (5H, singlet, $C_6H_5$).

(b) The whole (1.52 g=5.2 mmole) of the methyl 3(S)-benzyloxycarbonylamino-5-methylhexanoate produced as described in step (a) was reduced by the method of Hamada and Shioiri [Tetrahedron Letters 23, 1193 (1982)] with lithium chloride-sodium borohydride, and then purified by silica gel column chromatography (eluent:methylene chloride). There were obtained 1.2 g. of an alcohol product, 3(S)-benzyloxycarbonylamino-5-methylhexanol, as a syrup.

Nuclear magnetic resonance spectrum ($CDCl_3$) δ ppm:

0.90 (6H, doublet, J=6 Hz, C$\underline{H}_3$);
1.05–2.12(5H, multiplet, —C$\underline{H}$, —C$\underline{H}_2$—, —C$\underline{H}_2CH_2OH$);
3.03–3.37(1H, broad, O$\underline{H}$);
3.39–4.20(3H, multiplet, C$\underline{H}_2$OH, NHC$\underline{H}$);
4.48–4.93(1H, broad, N$\underline{H}$);
5.08(2H, singlet, $C_6H_5$—C$\underline{H}_2$);
7.35(5H, singlet, $C_6H_5$).

(c) To a solution of 0.5 g. (1.9 mmole) of 3(S)-benzyloxycarbonylamino-5-methylhexanol in 20 ml. of methanol were added 3.8 ml. of 1N hydrochloric acid. The mixture was subjected to catalytic reduction by bubbling hydrogen through the mixture in the presence of a 10% w/w palladium-on-carbon catalyst. After 1.5 hours, the catalyst was removed by filtration, and the solvent was removed from the filtrate by distillation under reduced pressure. To an ice-cooled solution of the residue in 5 ml. of methylene chloride was added N-methylmorpholine. To the mixture was added an active ester solution of $N^\alpha$-t-butyroxycarbonyl-$N^{im}$-2,4-dinitrophenyl-L-histidine, prepared from 0.92 g. (1.9 mmole) of $N^\alpha$-t-butyroxycarbonyl-$N^{im}$-2,4-dinitrophenyl-L-histidine isopropanol, 0.25 g. (2.1 mmole) of 1-hydroxybenztriazole and 0.47 g. (2.3 mmole) of DCC. The resulting mixture was stirred at room temperature for 20 hours and then treated in a conventional manner to give a partially crystallized syrup; to this was added diethyl ether. The inside of the vessel containing the mixture was scratched and the resulting crystals were separated by filtration. There was obtained 0.95 g. of $N^\alpha$-t-butyroxycarbonyl-$N^{im}$-2,4-dinitrophenyl-L-histidyl-3(S)-amino-5-methylhexanol as yellow crystals melting at 112°–114° C.

To 0.53 g. (1 mmole) of this product were added 0.11 g. of anisole and 6 ml. of trifluoroacetic acid (TFA). The mixture was then stirred at room temperature for 25 minutes. The TFA was then removed by distillation and anhydrous diethyl ether was added to the residue to form a precipitate, which was separated by filtration. To a solution of the precipitate in dimethylformamide was added, whilst cooling with ice, 0.11 g. of N-methylmorpholine, followed by 0.44 g. (1.1 mmole) of N-benzyloxycarbonyl-L-phenylalanine hydroxysuccinimide. The mixture was stirred at room temperature for 3 hours and then treated in a conventional manner. There was obtained 0.62 g. of N-benzyloxycarbonyl-L-phenylalanyl-$N^{im}$-2,4-dinitrophenyl-L-histidyl-3(S)-amino-5-methylhexanol, melting at 163°–167° C.

Elemental analysis: Calculated for $C_{36}H_{40}O_9N_7.2H_2O$: C, 57.60%; H, 5.91%; N, 13.06%. Found: C, 57.75%; H, 5.58%; N, 13.01%.

(d) 0.43 mg. (0.6 mmole) of the alcohol prepared as described in step (c) was oxidized according to the method of Hamada and Shioiri [Chem. Pharm. Bull., 30, 1921 (1982)] with pyridine-sulphur trioxide in pyridine. The oxidation product was purified by silica gel column chromatography (eluent: chloroform/ethanol/acetic acid=95:5:3 by volume). There was obtained 0.27 g. of N-benzyloxycarbonyl-L-phenylalanyl-$N^{im}$-2,4-dinitrophenyl-L-histidyl-3(S)-amino-5-methylhexanol. To a solution of 143 mg. (0.2 mmole) of this product in 5 ml. of methanol were added 78 mg. (1 mmole) of 2-mercaptoethanol. The mixture was adjusted to a pH of 8 by the addition of a 5% w/v aqueous solution of sodium bicarbonate and stirred at room temperature for 2 hours. The solvent was then removed by distillation under reduced pressure, and the resulting residue was dissolved in ethyl acetate. The solution was washed with water, dried and concentrated by evaporation under reduced pressure. To the residue was added a 2:1 by volume mixture of diethyl ether and ethyl acetate, to form a precipitate, which was separated by filtration. There were obtained 75 mg. of the desired compound as a white powdery solid, melting at 173°–175° C.; $[\alpha]^{22} -20.2°$ (C=0.5, methanol).

Elemental analysis: Calculated for $C_{30}H_{37}O_5N_5.5H_2O$: C, 56.50%; H, 7.42%; N, 10.98%. Found: C, 56.18%; H, 7.56%; N, 10.98%.

EXAMPLE 7

N-(2-Benzyloxycarbonyl-1,2,3,4-tetrahydro-β-carbolin-3-ylcarbonyl)-L-histidyl-L-leucinal(Compound No. 7)

The procedure described in Example 1(a) was repeated, but using 125 mg. (0.25 mmole) of N-(2-benzyloxycarbonyl-1,2,3,4-tetrahydro-β-carbolin-3-ylcarbonyl)-L-histidine hydrazide. There were obtained 120 mg. of N-(2-benzyloxycarbonyl-1,2,3,4-tetrahydro-β-carbolin-3-ylcarbonyl)-L-histidyl-L-leucinal semicarbazone. This product was then treated in the same way as in Example 1(b) by partition chromatography using Sephadex G-25, to give 67 mg. of the desired compound as a white powdery solid, melting at 126°–130° C.; $[\alpha]^{22} +21.6°$ (C'0.5, methanol).

Elemental analysis: Calculated for $C_{32}H_{35}O_6N.\frac{1}{2}H_2O$: C, 63.15%; H, 5.96%; N, 13.81%. Found: C, 63.42%; H, 5.73%; N, 13.65%.

EXAMPLE 8

N-Benzyloxycarbonyl-L-phenylalanyl-L-histidyl-L-leucinol(Compound No. 10)

To a solution of 0.91 g. (2 mmole) of N-benzyloxycarbonyl-L-phenylalanyl-L-histidine hydrazide in 32 ml. of dimethylformamide was added 1.64 ml. of a 4.1N solution of hydrogen chloride in dioxane. The mixture was cooled to −60° C., and there was added 0.4 ml. of isopentyl nitrite. The temperature of the resulting mixture was then raised to −20° C. After confirming the disappearance of the hydrazide, the temperature of the mixture was lowered to −60° C., and then the mixture was neutralized by the addition of 0.8 g. of N-methylmorpholine. To the mixture was added 0.28 g. (2.4 mmole) of L-leucinol and the mixture was stirred at 4° C. for 23 hours; the solvent was then removed by distillation under reduced pressure, and water was added to the residue to form a colourless precipitate, which was separated by filtration and washed thoroughly with water and then with ethyl acetate. There was obtained 0.94 g. of the desired compound as a white powdery solid, melting at 181°–183° C.; $[\alpha]^{22} -19.4°$ (C=0.5, methanol).

Elemental analysis: Calculated for $C_{29}H_{37}O_5N_5$: C, 65.02%; H, 6.96%; N, 13.08%. Found: C, 64.62%; H, 7.06%; N, 13.04%.

EXAMPLE 9

N-Benzyloxycarbonyl-3-(1-naphthyl)-L-alanyl-L-histidyl-L-leucinol(Compound No. 14)

The procedure described in Example 8 was repeated, but using 0.25 g. (0.5 mmole) of N-benzyloxycarbonyl-3-(1-naphthyl)-L-alanyl-L-histidine hydrazide. There was obtained 0.22 g. of the desired compound as a white powdery solid, melting at 163°–165° C.; $[\alpha]^{22} -56.2°$ (C=0.5, methanol).

Elemental analysis: Calculated for $C_{33}H_{39}O_5N_5.\frac{1}{4}H_2O$: C, 67.16%; H, 6.75%; N, 11.87%. Found: C, 67.04%; H, 6.80%; N, 11.36%.

EXAMPLE 10

N-[3-(3-Nitro-2-pyridyldithio)propionyl]-L-phenylalanyl-L-histidyl-L-leucinol (Compound No. 11)

To 0.16 g. (0.3 mmole) of N-benzyloxycarbonyl-L-phenylalanyl-L-histidyl-L-leucinol were added 3 ml. of a 25% w/v glacial acetic acid solution of hydrogen bromide. The mixture was stirred at room temperature for 30 minutes, and then anhydrous diethyl ether was added thereto. The precipitate thus formed was separated by filtration and dissolved in 5 ml. of dimethylformamide. The solution was cooled with ice, and then there were added 30 mg. of N-methylmorpholine for neutralization. To the neutralized solution were added an active ester prepared from 86 mg. (0.33 mmole) of 3-(3-nitro-2-pyridyldithio)propionic acid, 39 mg. (0.33 mmole) of 1-hydroxybenztriazole and 74 mg. (0.36 mmole) of DCC. The mixture was stirred for 1 hour whilst cooling with ice and then overnight at room temperature, after which it was treated in a conventional manner to give a yellow powder, which was purified by silica gel column chromatography (eluent: chloroform/methanol=8:1 by volume), to afford 47 mg. of the desired compound as a yellow powdery solid, melting at 109°–112° C.; $[\alpha]^{22}$ −33.8° (C=0.5, methanol).

Elemental analysis: Calculated for $C_{29}H_{37}O_6N_7S_2$: C, 54.11%; H, 5.79%; N, 15.23%; S, 9.96%. Found: C, 53.90%; H, 5.92%; N, 15.34%; S, 9.72%.

EXAMPLE 11

N-t-Butoxycarbonyl-S-(3-nitro-2-pyridylthio)-L-cysteinyl-L-histidyl-L-leucinol

The procedure described in Example 10 was repeated, but using 143 mg. (0.3 mmole) of N-t-butoxycarbonyl-S-(3-nitro-2-pyridylthio)-L-cysteine. There were obtained 90 mg. of the desired compound as a yellow powdery solid, melting at 185°–188° C.; $[\alpha]^{22}$ −39.4° (C=0.5, methanol).

Elemental analysis: Calculated for $C_{35}H_{46}O_8N_8S_2$: C, 54.53%; H, 6.01%; N, 14.53%; S, 8.32%. Found: C, 54.75%; H, 6.23%; N, 14.34%; S, 8.16%.

EXAMPLE 12

(2S,3S)-3-[N-Benzyloxycarbonyl-L-phenylalanyl-L-histidyl]amino-2-hydroxy-5-methylhexanol

(a) Methyl (2S,3S)-3-t-butoxycarbonylamino-2-hydroxy-5-methylhexanoate

To a solution of 1.00 g (3.8 mmole) of (2S,3S)-3-(t-butoxycarbonyl)amino-2-hydroxy-5-methylhexaneoic acid prepared according to the method of R. L. Johnson [J. Med. Chem., 25, 605 (1982)] in 30 ml. of methanol was added, with stirring and ice-cooling, an ethereal solution of diazomethane. The mixture was stirred at room temperature for 1 hour. The solvent was removed by distillation, and the solid thus obtained was recrystallized from hexane, to afford 952 mg. of colourless needles, melting at 84°–85° C.; $[\alpha]^{22}$ −10.2° (C=1.26, methanol).

Elemental analysis: Calculated for $C_{13}H_{25}NO_5$: C, 56.71%; H, 9.15%; N, 5.08%. Found: C, 56.57%; H, 9.09%; N, 4.97%.

Nuclear magnetic resonance spectrum (CDCl$_3$) δ ppm:
0.91 (6H, doublet, J=7.5 Hz, C$\underline{H}_3\times 2$);
1.45 (9H, singlet, t-Bu);
3.17(1H, doublet, J=6 Hz, O$\underline{H}$);
3.80 (3H, singlet, OCH$_3$);
3.90–4.27 (1H, multiplet, NHC$\underline{H}$);
4.35 (1H, doubled doublet, J=3 Hz, and J=6 Hz, C$\underline{H}$CO$_2$CH$_3$);
4.53–4.96 (1H, multiplet, N$\underline{H}$).
Mass analysis: m/e 275 (M$^+$).

Infrared absorption spectrum (Nujol-trade markmull) $\nu_{max}$ cm.$^{-1}$: 3375 (OH), 1740 (ester CO).

(b) (2S,3S)-3-t-Butoxycarbonylamino-2-hydroxy-5-methylhexanol

To a suspension of 305 mg. (8.07 mmole) of sodium borohydride and 342 mg. (8.07 mmole) of lithium chloride in 20 ml. of a 3:2 by volume mixture of ethanol and tetrahydrofuran were added 740 mg. (2.69 mmole) of the hydroxymethyl ester prepared as described in step (a). The mixture was stirred at room temperature for 4 hours, and then the solution was concentrated by evaporation under reduced pressure. To the concentrate were added 20 ml. of water, and the mixture was extracted with ethyl acetate. The extract was dried over anhydrous sodium sulphate, and the solvent was removed by distillation under reduced pressure. The solid thus obtained was recrystallized from petroleum ether, to afford 516 mg. of colourless needles, melting at 58°–59° C.; $[\alpha]^{25}$ −26.2° (C=0.91, methanol).

Elemental analysis: Calculated for $C_{12}H_{25}NO_4$: C, 58.28%; H, 10.19%; N, 5.66%. Found: C, 58.04%; H, 10.10%; N, 5.54%.

Mass analysis: m/e 247 (M$^+$).

Infrared absorption spectrum (Nujol mull) $\nu_{max}$ cm$^{-1}$: 3375 (OH).

(c)

An azide solution was prepared in the same way as described in Example 8, using 0.45 g. (1 mmole) of N-benzyloxycarbonyl-L-phenylalanyl-L-histidine hydrazide.

Meanwhile, the protecting group was removed from 0.25 g. (1.1 mmole) of (2S,3S)-3-t-butoxycarbonylamino-2-hydroxy-5-methylhexanol by treatment with TFA in the presence of 0.11 g. of anisole, and then anhydrous diethyl ether was added to form a precipitate, which was dissolved in 5 ml. of dimethylformamide. To the solution was added 0.11 g. of N-methylmorpholine for neutralization. The solution thus obtained was added to the azide solution obtained above and the mixture was stirred overnight at 4° C. and then treated in a conventional manner, to give 0.46 g. of the desired compound as a white powdery solid, melting at 159°–162° C.; $[\alpha]^{22}$ −30.0° (C=0.5, methanol).

Elemental analysis: Calculated for $C_{30}H_{39}O_6N_5$: C, 63.69%; H, 6.95%; N, 12.38%. Found: C, 63.47%; H, 7.05%; N, 12.40%.

EXAMPLE 13

1(R)-(N-Benzyloxycarbonyl-L-phenylalanyl-L-histidyl)amino-3-methylbutylphosphonic acid An azide solution was prepared in the same way as in Example 8 using 0.45 g. (1 mmole) of N-benzyloxycarbonyl-L-phenylalanyl-L-histidine hydrazide. To the solution was added 0.20 g. (1 mmole) of 1(R)-amino-3-methylbutylphosphonic acid hemihydrochloride (melting at 267°–269.5°) prepared according to the method of J. R. Chambers and A. F. Isbell [J. Org. Chem., 29, 832 (1964)], followed by 0.11 g. of N-methylmorpholine. The mixture was stirred at 4° C. for 11 days. Insoluble matter was removed by filtration and the filtrate was treated in a conventional manner. There was obtained 0.47 g. of the desired compound as a white powdery solid, melting at 159°–167° C.; $[\alpha]^{22}$ −15.6° (C=0.5, dimethylformamide).

Elemental analysis: Calculated for $C_{33}H_{48}O_9N_6P_2 \cdot \frac{1}{2}H_2O$: C, 56.56%; H, 6.27%; N, 11.77%; P, 5.21%. Found: C, 56.32%; H, 6.30%; N, 11.59%; P, 4.77%.

EXAMPLE 14

(2S,3S)-3-[N-Benzyloxycarbonyl-3-(1-naphthyl)-L-alanyl-L-histidyl]amino-2-hydroxy-5-methylhexanol The procedure described in Example 12(c) was repeated, but using 125 mg. (0.25 mmole) of N-benzyloxycarbonyl-3-(1-naphthyl)-L-alanyl-L-histidine hydrazide. There were obtained 47 mg. of the desired compound as a white powdery solid, melting at 176°–178° C.; $[\alpha]^{24}$ −57.4° (C=0.5, methanol).

Elemental analysis: Calculated for $C_{34}H_{41}N_5O_6$: C, 66.32%; H, 6.71%; N, 11.38%. Found: C, 66.01%; H, 6.92%; N, 11.15%.

EXAMPLE 15

(3S,4S)-4-[N-Benzyloxycarbonyl-3-(1-naphthyl)-L-alanyl-L-histidyl]amino-3-hydroxy-6-methylheptanol

(a)
(3S,4S)-4-t-Butoxycarbonylamino-3-hydroxy-6-methylheptanol

A solution of 1.0 g. (3.3 mmole) of ethyl (3S,4S)-4-t-butoxycarbonylamino-3-hydroxy-6-methylheptanoate prepared according to the method of D. Rich [J. Org. Chem., 43, 3624 (1978)] in 10 ml. of a 3:2 by volume mixture of ethanol and tetrahydrofuran was added to a suspension of 375 mg. (9.9 mmole) of sodium borohydride and 420 mg. (9.9 mmole) of lithium chloride in 30 ml. of a 3:2 by volume mixture of ethanol and tetrahydrofuran. The mixture was stirred overnight at room temperature, and then the excess reagents were decomposed with acetone. The solution was then concentrated by evaporation under reduced pressure, and water was added to the residue. The mixture was extracted with ethyl acetate, and the extract was dried over anhydrous sodium sulphate and then concentrated by evaporation under reduced pressure. The residue was purified by silica gel column chromatography (eluent: benzene/ethyl acetate). There were obtained 766 mg. of the desired product as an oil, $[\alpha]^{25}$ −38.2° (C=0.92, methanol).

Mass analysis $C_{13}H_{27}NO_4$: Calculated 261.1940; Found 261.1959 (M+).

(b)
(3S,4S)-4-[N-Benzyloxycarbonyl-3-(1-naphthyl)-L-alanyl-L-histidyl]amino-3-hydroxy-6-methylheptanol The procedure described in Example 12(c) was repeated, but using 125 mg. (0.25 mmole) of N-benzyloxycarbonyl-3-(1-naphthyl)-L-alanyl-L-histidine hydrazide and 65 mg. (0.25 mmole) of the alcohol prepared as described in (a) above. There were obtained 42 mg. of the desired compound as a white powdery solid, melting at 196°–198° C.; $[\alpha]^{24}$ −57.8° (C=0.5, methanol).

Elemental analysis: Calculated for $C_{35}H_{43}N_5O_6$: C, 66.75%; H, 6.88%; N, 11.12%. Found: C, 66.52%; H, 6.93%; N, 11.35%.

EXAMPLE 16

(3S,4S)-4-[N-Benzyloxycarbonyl-3-(1-naphthyl)-L-alanyl-L-histidyl]amino-3-hydroxy-6-methylheptanal (Compound No. 8)

(a) Ethyl (3S,4S)-3-t-butyldimethylsilyloxy-4-t-butyroxycarbonylamino-6-methylheptanoate To a solution of 2.0 g. (6.59 mmole) of ethyl (3S,4S)-t-butyroxycarbonylamino-3-hydroxy-6-methylheptanoate and 1.77 g. (16.5 mmole) of 2,6-lutidine in 5 ml. of dry methylene chloride cooled to 0° C. were added 2.61 g. (9.87 mmole) of t-butyldimethylsilyl trifluoromethanesulphonate. The mixture was stirred at room temperature for 20 minutes, and then 20 ml. of water were added. The mixture was then extracted with ethyl acetate, and the extract was washed successively with a 10% w/v aqueous solution of citric acid, water, a saturated aqueous solution of sodium bicarbonate and a saturated aqueous solution of sodium chloride and dried over anhydrous sodium sulphate. The solvent was removed by distillation under reduced pressure, and the liquid substance thus obtained was purified by silica gel column chromatography (eluent:hexane/ethyl acetate). There were obtained 2.25 g. of a colourless liquid, $[\alpha]^{25}$ −35.1° (C=1.16, methanol).

Mass analysis $C_{21}H_{43}NO_5Si$: Calculated 418.2988 (M+1)+; Found 418.2943.

(b)
(3S,4S)-4-t-Butyroxycarbonylamino-3-hydroxy-6-methylheptanal semicarbazone To a solution of 642 mg. (1.54 mmole) of the compound prepared as described in step (a) above in 7 ml. of anhydrous toluene prepared under nitrogen and cooled to −78° C. were added 3.8 ml. (3.8 mmole) of a 1M toluene solution of diisobutylaluminium hydride. The mixture was stirred at the same temperature for 6 minutes, and then to the resulting mixture was added 0.8 ml. of methanol, followed by an aqueous solution of potassium sodium tartarate and diethyl ether. The mixture was stirred, the organic layer was dried over anhydrous sodium sulphate, and the solvent was removed by distillation under reduced pressure. The unstable liquid thus obtained was promptly dissolved, without purification, in 5 ml. of 70% v/v aqueous ethanol, and to the solution were added 172 mg. (1.54 mmole) of semicarbazide hydrochloride and 152 mg. (1.85 mmole) of sodium acetate. The mixture was heated under reflux for 10 minutes, the solvent was then removed by distillation under reduced pressure, and ethyl acetate was added to the residue. The solution was washed successively with a saturated aqueous solution of sodium bicarbonate and a saturated aqueous solution of sodium chloride. The solvent was removed by distillation under reduced pressure, and the residue was promptly dissolved in 6 ml. of anhydrous tetrahydrofuran. To the solution were added 3 ml. (3 mmole) of a 1M tetrahydrofuran solution of tetrabutylammonium fluoride, and the mixture was stirred at room temperature for 30 minutes. To the resulting solution was added ethyl acetate, and the mixture was washed with a saturated aqueous solution of sodium chloride and dried over anhydrous sodium sulphate. The solvent was removed by distillation under reduced pressure, and the residue thus obtained was purified by thin-layer chromatography (developing solvent: ethyl acetate/methanol=10:1 by volume).

There were obtained 150 mg. of a colourless oily substance, which, on addition of ethyl acetate, solidified and was recrystallized from ethyl acetate/hexane, to afford colourless crystals, melting at 153°–155° C.; $[\alpha]^{24}$ −30.9° (C=0.35, methanol).

Elemental analysis: Calculated for $C_{14}H_{28}N_4O_4$: C, 53.14%; H, 8.92%; N, 17.72%. Found: C, 52.84%; H, 8.75%; N, 17.30%.

(c)

The N-t-butyroxycarbonyl group was removed from 95 mg. (0.3 mmole) of the compound prepared as described in step (b) above. The resulting product was reacted with the azide separately prepared from 150 mg. (0.3 mmole) of N-benzyloxycarbonyl-3-(1-naphthyl)-L-alanyl-L-histidine hydrazide and subsequently treated in the same way as described in Example 1. There were obtained 82 mg. of the desired compound as a white powdery solid, melting at 166°–168° C.; $[\alpha]^{24}$ −65.2° (C=0.5, dimethylformamide).

Elemental analysis: Calculated for $C_{35}H_{41}N_5O_6$: C, 66.96%; H, 6.58%; N, 11.16%. Found: C, 67.25%; H, 6.75%; N, 11.03%.

EXAMPLE 17

3(S)-[N-Benzyloxycarbonyl-3-(1-naphthyl)-L-alanyl-L-histidyl]amino-5-methylhexanal A mixed acid anhydride prepared in a conventional manner from 0.35 g. (1 mmole) of N-benzyloxycarbonyl-3-(1-naphthyl)-L-alanine was added at 0° C. to 5 ml. of a dimethylformamide solution of 3(S)-[$N^{im}$-2,4-dinitrophenyl-L-histidyl]amino-5-methylhexanol prepared from 0.53 g. (1 mmole) of 3(S)-[N-t-butyroxycarbonyl-$N^{im}$-2,4-dinitrophenyl-L-histidyl]-amino-5-methylhexanol by removal of the N-t-butyroxycarbonyl group by a conventional method. The mixture was stirred at the same temperature for 1 hour and then at room temperature overnight. The resulting mixture was then concentrated by evaporation under reduced pressure, and water was added to the residue. The yellow oily substance thus precipitated was extracted with ethyl acetate, and the organic layer was washed successively with a 5% w/v aqueous solution of sodium bicarbonate and a saturated aqueous solution of sodium chloride, dried over anhydrous sodium sulphate and concentrated by evaporation under reduced pressure. The oily residue was purified by silica gel column chromatography (eluent: chloroform/methanol=10:1 by volume). There was obtained 0.34 g. of 3(S)-[N-benzyloxycarbonyl-3-(1-naphthyl)-L-alanyl-$N^{im}$-2,4-dinitrophenyl-L-histidyl]amino-5-methylhexanol as a yellow powdery solid, melting at 119°–122° C. The same reaction and treatment as in Example 6(c) were then carried out with 0.34 g. (0.44 mmole) of this product, to give 43 mg. of the desired compound as a white powdery solid, melting at 153°–156° C.; $[\alpha]^{24}$ −45.2° (C=0.5, methanol).

Elemental analysis: Calculated for $C_{34}H_{39}N_5O_5$: C, 68.32%; H, 6.58%; N, 11.72%. Found: C, 68.61%; H, 6.35%; N, 11.89%.

EXAMPLE 18

N-Benzyloxycarbonyl-3-(2-naphthyl)-L-alanyl-L-histidyl-L-leucinal

The procedure described in Example 1 was repeated, but using 250 mg. (0.5 mmole) of N-benzyloxycarbonyl-3-(2-naphthyl)-L-alanyl-L-histidine hydrazide and 127 mg. (0.5 mmole) of L-leucinal semicarbazone hydrobromide. There were obtained 80 mg. of the desired compound as a white powdery solid, melting at 110°–112° C.; $[\alpha]^{24}$ −3.2° (C=0.5, methanol).

Elemental analysis: Calculated for $C_{33}H_{37}N_5O_5$: C, 67.90%; H, 6.39%; N, 12.00%. Found: C, 68.21%; H, 6.15%; N, 11.79%.

EXAMPLE 19

3-(1-Naphthyl)-L-alanyl-L-histidyl-L-leucinol dihydrobromide

To 0.59 g. (1 mmole) of N-benzyloxycarbonyl-3-(1-naphthyl)-L-alanyl-L-histidyl-L-leucinol (prepared as described in Example 9) were added 10 ml. of a 25% w/v hydrogen bromide/acetic acid solution. The mixture was stirred at room temperature for 30 minutes, after which there were added 100 ml. of anhydrous diethyl ether. The white precipitate thus formed was separated by filtration, thoroughly washed with diethyl ether and dried in a desiccator. There was obtained 0.52 g. of the desired compound as a white powdery solid, melting at 155°–159° C.; $[\alpha]^{24}$ +21.0° (C=0.5, methanol).

Elemental analysis: Calculated for $C_{25}H_{33}N_5O_3 \cdot 2HBr$: C, 48.95%; H, 5.75%; N, 11.42%; Br, 26.05%. Found: C, 49.23%; H, 5.83%; N, 11.15%; Br, 26.31%.

EXAMPLE 20

[N-Benzyloxycarbonyl-3-(1-naphthyl)-L-alanyl]-[3-(1-naphthyl)-L-alanyl]-L-histidyl-L-leucinol 70 mg. (0.2 mmole) of N-benzyloxycarbonyl-3-(1-naphthyl)-L-alanine and 40 mg. (0.22 mmole) of N-hydroxy-5-norbornene-2,3-dicarboximide were dissolved in 2 ml. of methylene chloride. The solution was cooled to 0° C., and there were then added 50 mg. (0.24 mmole) of dichlorohexylcarbodiimide; the mixture was stirred at 0° C. for 1 hour. The resulting solution was added to a cooled solution prepared from 5 ml. of a dimethylformamide solution of 123 mg. (0.2 ml.) of 3-(1-naphthyl)-L-alanyl-L-histidyl-L-leucinol dihydrobromide by neutralization with 20 mg. (0.2 mmole) of N-methylmorpholine. The mixture was stirred overnight at room temperature. The dicyclohexylurea precipitated was removed by filtration, and the filtrate was concentrated by evaporation under reduced pressure. To the residue was added a 5% w/v aqueous solution of sodium bicarbonate, and the oily substance thus formed was extracted with ethyl acetate. The organic layer was washed successively with water and with a saturated aqueous solution of sodium chloride, dried over anhydrous sodium sulphate and concentrated by evaporation under reduced pressure. When a small amount of water was added to the residual syrup, it solidified and was separated by filtration. This product (143 mg) was then purified by silica gel column chromatography (eluent: chloroform/methanol 10:1 by volume) to afford 55 mg. of the desired compound as a white powdery solid, melting at 199°–200° C.; $[\alpha]^{24}$ −81.6° (C=0.5, methanol).

Elemental analysis: Calculated for $C_{46}H_{50}N_6O_6$: C, 70.57%; H, 6.44%; N, 10.73%. Found: C, 70.75%; H, 6.65%; N, 10.52%.

EXAMPLE 21

N-α-Naphthoxyacetyl-3-(1-naphthyl)-L-alanyl-L-histidyl-L-leucinol

The procedure described in Example 20 was repeated but using 44 mg. (0.22 mmole) of α-naphthoxyacetic acid. There were obtained 90 mg. of the desired compound, melting at 215°–217° C.; $[\alpha]^{24}$ −61.0° (C=0.5, methanol).

Elemental analysis: Calculated for $C_{37}H_{41}N_5O_5$: C, 69.90%; H, 6.50%; N, 11.02%. Found: C, 70.12%; H, 6.65%; N, 10.87%.

EXAMPLE 22

N-Benzyloxycarbonyl-3-(1-naphthyl)-D-alanyl-L-histidyl-L-leucinol (a)

$N^\alpha$-t-Butyroxycarbonyl-$N^{im}$-2,4-dinitrophenyl-L-histidyl-L-leucinol 3.13 g. (6.5 mmole) of $N^\alpha$-t-butyroxycarbonyl-$N^{im}$-2,4-dinitrophenyl-L-histidine isopropanol and 1.28 g. (7.2 mmole) of N-hydroxy-5-norbornene-2,3-dicarboximide were dissolved in 25 ml. of methylene chloride. The solution was cooled to 0° C., and 1.55 g. (7.5 mmole) of dicyclohexylcarbodiimide dissolved in a small amount of methylene chloride were added. The mixture was stirred at 0° C. for 1 hour, and then 0.76 g. (6.5 mmole) of L-leucinol was added. The mixture was stirred at room temperature for 18 hours. The dicyclohexylurea precipitated was removed by filtration, and the filtrate was concentrated by evaporation under reduced pressure. Water was added to the residue, and the yellow oily substance thus formed was extracted with ethyl acetate. The organic layer was washed successively with a 10% w/v aqueous solution of citric acid, water, a 5% w/v aqueous solution of sodium bicarbonate and a saturated aqueous solution of sodium chloride and then dried over anhydrous sodium sulphate. The solvent was removed by distillation under reduced pressure, and the residue was triturated with diethyl ether/petroleum ether to solidify it. The solidified mass was separated by filtration to afford 2.8 g. of the title compound, melting at 71°–78° C.

Elemental analysis: Calculated for $C_{23}H_{32}N_6O_8$: C, 53.07%; H, 6.20%; N, 16.15%. Found: C, 53.35%; H, 6.03%; N, 15.97%.

(b)

N-Benzyloxycarbonyl-3-(1-naphthyl)-D-alanyl-$N^{im}$-2,4-dinitrophenyl-L-histidyl-L-leucinol A mixed acid anhydride was prepared in a conventional manner from 186 mg. (0.53 mmole) of N-benzyloxycarbonyl-3-(1-naphthyl)-D-alanine. Separately, 360 mg. (0.7 mmole) of N-t-butyroxycarbonyl-$N^{im}$-2,4-dinitrophenyl-L-histidyl-L-leucinol was treated with 6 ml. of trifluoroacetic acid in the presence of 80 mg. (0.7 mmole) of anisole at room temperature for 30 minutes. To the resulting mixture were added 100 ml. of diethyl ether, and the yellow powder thus precipitated was separated by filtration and dissolved in 5 ml. of dimethylformamide. The solution was cooled to 0° C. and neutralized with 70 mg. (0.7 mmole) of N-methyl-morpholine; to the mixture was added the above-prepared mixed acid anhydride. The mixture was stirred at 0° C. for 1 hour, allowed to stand overnight at room temperature and then concentrated by evaporation under reduced pressure. To the residue was added dilute hydrochloric acid, and the yellow oily substance formed was extracted with ethyl acetate. The organic layer was washed successively with water, a 5% w/v aqueous solution of sodium bicarbonate and a saturated aqueous solution of sodium chloride and dried over anhydrous sodium sulphate. The solvent was removed by distillation under reduced pressure, and water was added to the residue to solidify it. The solidified mass was pulverized and separated by filtration, to afford 330 mg. of the title compound, which was used for the next reaction without purification.

(c)

N-Benzyloxycarbonyl-3-(1-naphthyl)-D-alanyl-L-histidyl-L-leucinol

To a solution of 150 mg. (0.2 mmole) of the compound prepared as described in step (b) in 5 ml. of methanol were added 150 mg. (2 mmole) of 2-mercaptoethanol. The pH of the mixture was adjusted to a value of 8 with a 5% w/v aqueous solution of sodium bicarbonate. The mixture was then stirred at room temperature for 2 hours, after which the solvent was removed by distillation under reduced pressure, and the residue was mixed with water and extracted with ethyl acetate. The organic layer was washed with a saturated aqueous solution of sodium chloride, dried over anhydrous sodium sulphate and concentrated by evaporation under reduced pressure. The residue was purified by silica gel column chromatography (eluent: chloroform/methanol=10:1 by volume), to afford 43 mg. of the desired compound as a white powdery solid, melting at 157°–159° C.; $[\alpha]^{24}$ +4.8° (C=0.5, methanol).

Elemental analysis: Calculated for $C_{33}H_{39}N_5O_5$: C, 67.67%; H, 6.71%; N, 11.96%. Found: C, 67.90%; H, 6.56%; N, 11.72%.

EXAMPLE 23

3-(1-Naphthyl)-D-alanyl-L-histidyl-L-leucinol.dihydrobromide

The procedure described in Example 19 was repeated, but reacting 0.59 g. (1 mmole) of the compound prepared as described in Example 22(c) with a 25% w/v hydrogen bromide/acetic acid solution to remove the benzyloxycarbonyl group. There was obtained 0.48 g. of the desired compound, melting at 153°–156° C.; $[\alpha]^{24}$ −51.0 (C=0.5, methanol).

Elemental analysis: Calculated for $C_{25}H_{33}N_5O_3.2HBr$: C, 48.95%; H, 5.75%; N, 11.42%; Br, 26.05%. Found: C, 49.05%; H, 5.89%; N, 11.09%; Br, 26.30%.

EXAMPLE 24

N-t-Butyroxycarbonyl-L-phenylalanyl-L-histidyl-L-leucinol (a)

N-t-Butyroxycarbonyl-L-phenylalanyl-$N^{im}$-2,4-dinitrophenyl-L-histidyl-L-leucinol The procedure described in Example 22(b) was repeated, but using 1.52 g. (4.2 mmole) of N-t-butyroxycarbonyl-L-phenylalanine hydroxysuccinimide. There was obtained 1.1 g. of the title compound as a yellow powdery solid, melting at 75°–85° C.

Elemental analysis: Calculated for $C_{32}H_{41}N_7O_9$: C, 57.56%; H, 6.19%; N, 14.68%. Found: C, 57.54%; H, 6.40%; N, 14.30%.

(b)

N-t-Butyroxycarbonyl-L-phenylalanyl-L-histidyl-L-leucinol

The procedure described in Example 22(c) was repeated, but using 200 mg. (0.3 mmole) of the compound prepared as described in step (a) above. There were obtained 43 mg. of the desired compound as a white powdery solid, melting at 115°–120° C.; $[\alpha]^{24}$ −28.0° (C=0.5, methanol).

Elemental analysis: Calculated for $C_{26}H_{39}N_5O_5.\frac{1}{2}H_2O$: C, 61.16%; H, 7.89%; N, 13.72%. Found: C, 61.48%; H, 7.75%; N, 13.71%.

EXAMPLE 25

N-(9-Fluorenylmethyloxycarbonyl)-3-(1-naphthyl)-L-alanyl-L-histidyl-L-leucinol (a)

N-(9-Fluorenylmethyloxycarbonyl)-3-(1-naphthyl)-L-alanyl-$N^{im}$-2,4-dinitrophenyl-L-hisdityl-L-leucinol The procedure described in Example 22(b) was repeated, but using 219 mg. (0.5 mmole) of N-(9-fluorenylmethyloxycarbonyl)-3-(1-naphthyl)-L-alanine. There were obtained 440 mg. of the title compound as a yellow powdery solid, melting at 118°–120° C.

(b)

N-(9-Fluorenylmethyloxycarbonyl)-3-(1-naphthyl)-L-alanyl-L-histidyl-L-leucinol

The procedure described in Example 22(c) was repeated, but using 170 mg. (0.2 mmole) of the compound prepared as described in step (a) above. There were obtained 50 mg. of the desired compound as a white powdery solid, melting at 160°–162° C.; $[\alpha]^{24}$ −71.4° (C=0.5, dimethylformamide).

Elemental analysis: Calculated for $C_{40}H_{41}N_5O_5$: C, 71.51%; H, 6.15%; N, 10.43%. Found: C, 71.40%; H, 6.32%; N, 10.27%.

EXAMPLE 26

N-Benzyloxycarbonyl-DL-4-nitrophenylalanyl-L-histidyl-L-leucinol (a)

N-Benzyloxycarbonyl-DL-4-nitrophenylalanyl-$N^{im}$-2,4-dinitrophenyl-L-histidyl-L-leucinol The procedure described in Example 22(b) was repeated, but using 0.34 g. (1 mmole) of N-benzyloxycarbonyl-DL-4-nitrophenylalanine. There was obtained 0.54 g. of the title compound as a yellow powdery solid, melting at 115°–118° C.

(b)

N-Benzyloxycarbonyl-DL-4-nitrophenylalanyl-L-histidyl-L-leucinol

The procedure described in Example 22(c) was repeated, but using 224 mg. (0.3 mmole) of the compound prepared as described in step (a) above. There were obtained 79 mg. of the desired compound, melting at 151°–154° C.; $[\alpha]^{24}$ −16.6° (C=0.5, methanol).

Elemental analysis: Calculated for $C_{29}H_{36}N_6O_7$: C, 59.98%; H, 6.25%; N, 14.48%. Found: C, 60.22%; H, 6.41%; N, 14.21%.

EXAMPLE 27

N-Benzyloxycarbonyl-DL-4-chlorophenylalanyl-L-histidyl-L-leucinol (a)

N-Benzyloxycarbonyl-DL-4-chlorophenylalanyl-$N^{im}$-2,4-dinitrophenyl-L-histidyl-L-leucinol The procedure described in Example 22(b) was repeated, but using 0.25 g. (0.74 mmole) of N-benzyloxycarbonyl-DL-4-chlorophenylalanine. There was obtained 0.35 g. of the title compound.

(b)

N-Benzyloxycarbonyl-DL-4-chlorophenylalanyl-L-histidyl-L-leucinol

The procedure described in Example 22(c) was repeated, but using 0.35 g. (0.48 mmole) of the compound prepared as described in step (a) above. There were obtained 125 mg. of the desired compound as a white powdery solid, melting at 153°–163° C.; $[\alpha]^{24}$ −13.8° (C=0.5, methanol).

Elemental analysis: Calculated for $C_{29}H_{36}N_5O_5Cl$: C, 61.10%; H, 6.37%; N, 12.28%; Cl, 6.22%. Found: C, 61.34%; H, 6.15%; N, 12.45%; Cl, 6.39%.

EXAMPLE 28

(−)-1-Benzyloxycarbonylamino-4-phenylbutyryl-L-histidyl-L-leucinol (a) L-Histidyl-L-leucinol dihydrochloride To a solution of 5.49 g. (10 mmole) of $N^{\alpha}$-t-butyroxycarbonyl-$N^{im}$-2,4-dinitrophenyl-L-histidyl-L-leucinol in 25 ml. of methanol were added 3.9 g. (50 mmole) of 2-mercaptoethanol. The pH of the mixture was adjusted to a value of 8 with a 5% w/v aqueous solution of sodium bicarbonate, and the mixture was stirred at room temperature for 3 hours. The solvent was removed by distillation under reduced pressure, and the residue was extracted with ethyl acetate. The organic layer was washed with water and dried over anhydrous sodium sulphate. The solvent was then removed by distillation under reduced pressure, and the residue was purified by silica gel column chromatography (eluent: chloroform/methanol). To the $N^{\alpha}$-t-butyroxycarbonyl-L-histidyl-L-leucinol thus obtained was added 20 ml. of a 6N hydrochloric acid/dioxane solution, and the mixture was stirred at room temperature for 30 minutes. 120 ml. of anhydrous diethyl ether were then added, and the white precipitate thus formed was separated by filtration, to afford 2.5 g. of the title compound as a white powdery solid, melting at 121°–123° C.

Elemental analysis: Calculated for $C_{12}H_{22}N_4O_2.2HCl.H_2O$: C, 41.74%; H, 7.54%; N, 16.23%; Cl, 20.54%. Found: C, 42.30%; H, 7.52%; N, 15.82%; Cl, 20.04%.

(b)

(−)-1-Benzyloxycarbonylamino-4-phenylbutyryl-L-histidyl-L-leucinol

To an azide prepared in a conventional manner from 327 mg. (1 mmole) of (−)-1-benzyloxycarbonylamino-4-phenylbutyric acid hydrazide were added 345 mg. (1 mmole) of L-histidyl-L-leucinol dihydrochloride, followed by 101 mg. (1 mmole) of N-methylmorpholine. The mixture was stirred overnight at 4° C. The solvent was removed by distillation under reduced pressure, and to the residue was added a 5% w/v aqueous solution of sodium bicarbonate. A white precipitate formed, and this was separated by filtration, thoroughly washed with water and dried over anhydrous sodium sulphate. The white powder thus obtained was purified by silica gel column chromatography (eluent: chloroform/methanol=20:1 and 10:1 by volume), to afford 220 mg. of the desired compound as a white powdery solid, melting at 178°–180° C.; $[\alpha]^{24}$ −16.0° (C=0.5, methanol).

Elemental analysis: Calculated for $C_{30}H_{39}N_5O_5 \cdot H_2O$: C, 63.47%; H, 7.28%; N, 12.34%. Found: C, 63.70%; H, 7.23%; N, 12.38%.

EXAMPLE 29

N-Benzyloxycarbonyl-L-phenylglycyl-L-histidyl-L-leucinol

A mixed acid anhydride prepared in a conventional manner from 286 mg. (1 mmole) of N-benzyloxycarbonyl-L-phenylglycine was added to a cooled solution of 345 mg. (1 mmole) of L-histidyl-L-leucinol dihydrochloride and 101 mg. (1 mmole) of N-methylmorpholine in 5 ml. of dimethylformamide. The mixture was stirred at 0° C. for 1 hour and at room temperature for an additional 3 hours. The solvent was removed by distillation under reduced pressure, and a 5% w/v aqueous solution of sodium bicarbonate was added to the residue. There was formed an oily substance, which was extracted with ethyl acetate. The ogranic layer was washed successively with water and with a saturated aqueous solution of sodium chloride, dried over anhydrous sodium sulphate and concentrated by evaporation under reduced pressure. The oily residue was purified by silica gel column chromatography (eluent: chloroform/methanol=20:1 by volume), to afford 166 mg. of the desired compound, melting at 162°–165° C.; $[\alpha]^{24}$ +13.4° (C=0.5, methanol).

Elemental analysis: Calculated for $C_{28}H_{35}N_5O_5 \cdot \frac{1}{2}H_2O$: C, 63.38%; H, 6.84%; N, 13.20%. Found: C, 63.49%; H, 6.68%; N, 13.04%.

EXAMPLE 30

N-Benzyloxycarbonyl-3-(1-naphthyl)-L-alanyl-L-histidyl-L-isoleucinol (Compound No. 24)

The procedure described in Example 8 was repeated, except that 150 mg. (0.3 mmole) of N-benzyloxycarbonyl-3-(1-naphthyl)-L-alanyl-L-histidyl hydrazide and 39 mg. (0.33 mmole) of L-isoleucinol were used. There were obtained 110 mg. of the desired product as a white powder, melting at 197°–199° C.; $[\alpha]^{24}$ −54.4° (C=0.5, methanol).

Elemental analysis: Calculated for $C_{33}H_{39}N_5O_5$: C, 67.67%; H, 6.71%; N, 11.96%. Found: C, 67.42%; H, 6.90%; N, 11.75%.

EXAMPLE 31

(3S,4S)-4-[N-Benzyloxycarbonyl-3-(1-naphthyl)-L-alanyl-L-histidyl]amino-3-hydroxy-6-methylheptanamide (Compound No. 25)

(a) To a solution of 250 mg. (0.5 mmole) of N-benzyloxycarbonyl-3-(1-naphthyl)-L-alanyl-L-histidine hydrazide in 8 ml. of dimethylformamide was added 0.42 ml. of a 4N solution of hydrochloric acid in dioxane, and the mixture was cooled to −60° C. 0.1 ml. of isopentyl nitrite was then added and the reaction temperature was raised to −20° C. After disappearance of the hydrazide had been confirmed, the temperature was lowered to −60° C. The mixture was neutralized with 0.17 g. of N-methylmorpholine to form a solution of N-benzyloxycarbonyl-3-(1-naphthyl)-L-alanyl-L-histidine azide.

(b) Meanwhile, a mixture of 137 mg. (0.5 mmole) of (3S,4S)-4-t-butoxycarbonylamino-3-hydroxy-6-methylheptanoic acid amide and 5 ml. of 6N hydrochoric acid in dioxane was stirred under a nitrogen atmosphere for 20 minutes and then evaporated under reduced pressure to dryness. The residue was dissolved in 2 ml. of dimethylformamide and 0.05 g. of N-methylmorpholine was then added to form a solution of (3S,4S)-4-amino-3-hydroxy-6-methylheptanamide.

(c) To the azide solution prepared in step (a) was added dropwise the amide solution prepared in step (b) and the resulting mixture was stirred at 4° C. for 20 hours. The solvent was then distilled off under reduced pressure, and a 5% w/v aqueous solution of sodium bicarbonate was added to the residue. A gummy solid separated and was extracted into ethyl acetate. The organic layer was washed with water and then with a saturated aqueous solution of sodium chloride, dried over anhydrous sodium sulphate and then concentrated by evaporation under reduced pressure. The residue solidified and was triturated with a 1:5 by volume mixture of ethyl acetate and diethyl ether and then filtered to give 129 mg. of the title product as a white powder, melting at 158°–161° C.; $[\alpha]^{23}$ −54.6° (C=0.5, methanol).

Elemental analysis: Calculated for $C_{35}H_{42}N_6O_6$: C, 65.40%; H, 6.59%; N, 13.08%. Found: C, 65.13%; H, 6.85%; N, 13.32%.

We claim:

1. Compounds of formula (I):

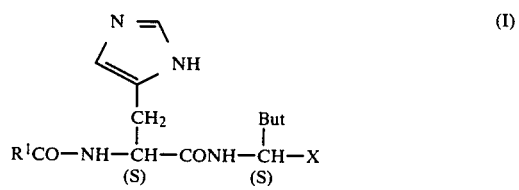

wherein:
R¹ represents a $C_1$–$C_4$ alkyl group having:
(a) an amino or protected amino substituent on its α-carbon atom and
(b) a phenyl or naphthyl group, a 5- or 6-membered heterocyclic group having one or more of hetero atoms selected from nitrogen, oxygen and sulfur atoms, a 3-indolinyl group or a 1,2,3,4-tetrahydro-β-carbolin-3-yl group, said R¹CO— having one or more substituents selected from an amino group and a protected amino group; or
R¹ represents a 1,2,3,4-tetrahydro-β-carbolin-3-yl group or a 1,2,3,4-tetrahydro-β-carbolin-1-yl group;
But represents a butyl group selected from the isobutyl and sec-butyl groups;
X represents
the formyl group or,
a group of formula —CH(R²)—Y wherein R² is a hydrogen atom, an alkyl group of 1 to 8 carbon atoms or a substituted alkyl group of 1 to 8 carbon atoms and having at least one substituent selected from a hydroxy, mercapto, amino, carbamoyl, formyl, phenyl, naphthyl or 5- or 6-membered heterocyclic group having one or more of hetero atoms of N, O and S, and Y is hydroxy, mercapto or formyl; and the carbon atoms marked with (S) are of the S-configuration;

provided that $R^1$ does not represent the benzyloxycarbonyl-L-phenylalanyl group or the benzyloxycarbonyl-L-prolyl-L-phenylalanyl group when X represents the formyl group;

and pharmaceutically acceptable salts and esters thereof.

2. Compounds as claimed in claim 1, having the formula (Ia):

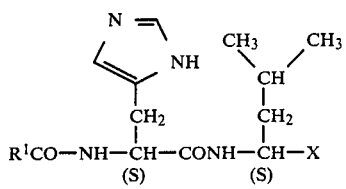

(in which $R^1$, X and S are as defined in claim 1).

3. Compounds as claimed in claim 1, having the formula (Ib):

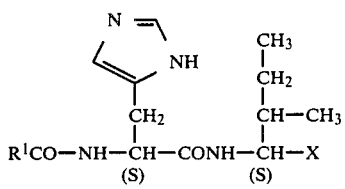

(in which $R^1$, X and S are as defined in claim 1).

4. Compounds as claimed in any one of claims 2, 3 or 1, wherein the acyl group represented by $R^1CO—$ is selected from the phenylalanyl, N-(benzyloxycarbonyl)phenylalanyl, alpha-(benzyloxycarbonylamino)-phenylacetyl, N-(4-phenylbutyryl)phenylalanyl, 2-hydroxy-3-phenylpropionyl, N-(benzyloxycarbonyl)-tyrosyl, N-(2-nitrophenylthio)phenylalanyl, N-(3-nitro-2-pyridylthio)phenylalanyl, 2-benzyloxycarbonylamino-3-(1-naphthoyl)propionyl, 2-benzyloxycarbonylamino-3-(2-naphthoyl)propionyl, N-benzyloxycarbonyl-3-(3-quinolyl)-L-alanyl and N-benzyloxycarbonyl-3-(8-quinolyl)-L-alanyl groups, and groups having the formulae:

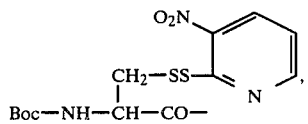

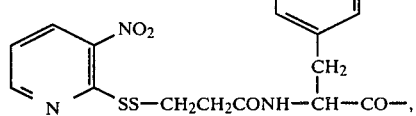

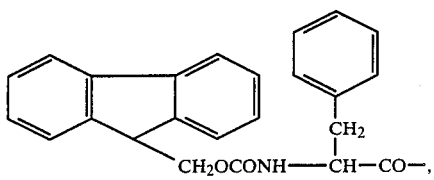

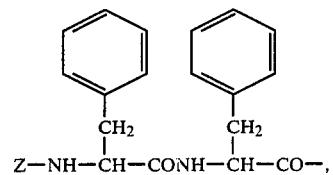

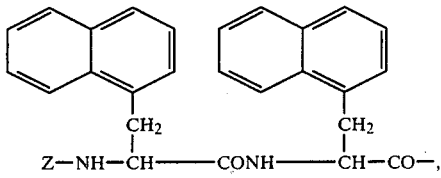

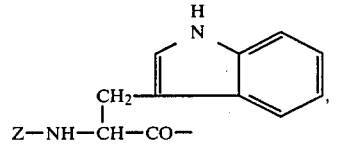

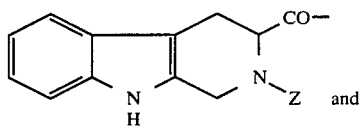

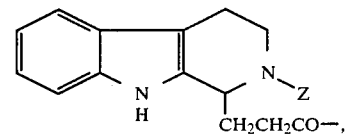

in which Boc represents the t-butoxycarbonyl group and Z represents the benzyloxycarbonyl group.

5. Compounds as claimed in any one of claims 2, 3 or 1, wherein the group represented by X is selected from the formyl, hydroxymethyl, formylmethyl, 2-formyl-1-hydroxyethyl, 1,2-dihydroxyethyl, 1,3-dihydroxypropyl, 2-hydroxy-1-mercaptoethyl groups and groups of formulae

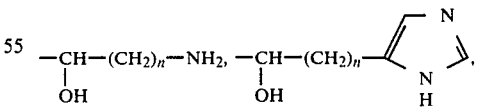

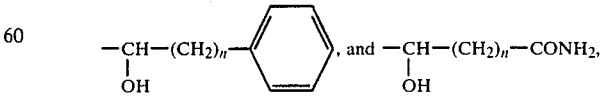

in which n represents an integer from 2 to 8.

6. Compounds as claimed in claim 1, selected from the group consisting of:
N-(4-phenylbutyryl)-L-phenylalanyl-L-histidyl-L-leucinal, N-[3-(3-nitro-2-pyridyldithio)propionyl]-L-phenylalanyl-L-histidyl-L-leucinal, N-benzyloxycarbonyl-3-(1-naphthyl)-L-alanyl-L-histidyl-L-leucinal, N-benzyloxycarbonyl-L-phenylalanyl-L-histidyl-L-leucinol, N-[3-(3-nitro-2-pyridyldithio)propionyl]-L-phenylalanyl-L-histidyl-L-leucinol, N-benzyloxycarbonyl-3-(1-naphthyl)-L-alanyl-L-histidyl-L-leucinol, and pharmaceutically acceptable salts and esters thereof.

7. N-(4-phenylbutyryl)-L-phenylalanyl-L-histidyl-L-leucinal of the formula of claim 1.

8. N-[3-(3-nitro-2-pyridyldithio)propionyl]-L-phenylalanyl-L-histidyl-L-leucinal of the formula of claim 1.

9. N-benzyloxycarbonyl-3-(1-naphthyl)-L-alanyl-L-histidyl-L-leucinal of the formula of claim 1.

10. N-benzyloxycarbonyl-L-phenylalanyl-L-histidyl-L-leucinol of the formula of claim 1.

11. N-[3-(3-nitro-2-pyridyldithio)propionyl]-L-phenylalanyl-L-histidyl-L-leucinol of the formula of claim 1.

12. N-benzyloxycarbonyl-3-(1-naphthyl)-L-alanyl-L-histidyl-L-leucinol of the formula of claim 1.

13. A method of treating angiotensin-induced hypertension in a mammal, by administering to said mammal an effective amount of a renin inhibitor, wherein said renin inhibitor is selected from the group consisting of compounds of formula (I):

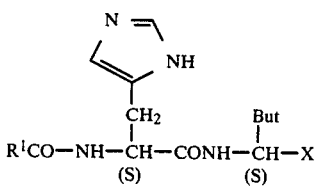

wherein:
$R^1$ represents a $C_1$-$C_4$ alkyl group having:
(a) an amino or protected amino substituent on its α-carbon atom and
(b) a phenyl or naphthyl group, a 5- or 6-membered heterocyclic group having one or more of hetero atoms selected from nitrogen, oxygen and sulfur atoms, a 3-indolinyl group or a 1,2,3,4-tetrahydro-β-carbolin-3-yl group, said $R^1CO$— having one or more substituents selected from an amino group and a protected amino group; or
$R^1$ represents a 1,2,3,4-tetrahydro-β-carbolin-3-yl group or a 1,2,3,4-tetrahydro-β-carbolin-1-yl group;
But represents a butyl group selected from the isobutyl and sec-butyl groups;
X represents
the formyl group or,
a group of formula —CH($R^2$)—Y
wherein $R^2$ is a hydrogen atom, an alkyl group of 1 to 8 carbon atoms or a substituted alkyl group of 1 to 8 carbon atoms and having at least one substituent selected from a hydroxy, mercapto, amino, carbamoyl, formyl, phenyl, naphthyl or 5- or 6-membered heterocyclic group having one or more of hetero atoms of N, O and S, and Y is hydroxy, mercapto or formyl; and the carbon atoms marked with (S) are of the S-configuration;
provided that $R^1$ does not represent the benzyloxycarbonyl-L-phenylalanyl group or the benzyloxycarbonyl-L-prolyl-L-phenylalanyl group when X represents the formyl group;
and pharmaceutically acceptable salts and esters thereof.

14. A method as claimed in claim 13, wherein said renin inhibitor is selected from compounds of formula (Ia):

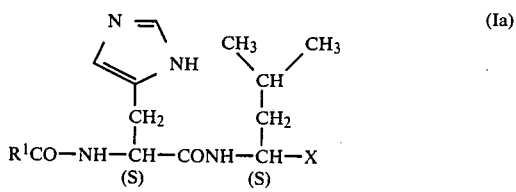

(in which $R^1$, X and S are as defined in claim 13) and pharmaceutically acceptable salts and esters thereof.

15. A method as claimed in claim 13, wherein said renin inhibitor is selected from compounds of formula (Ib):

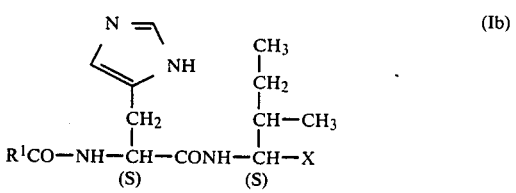

(in which $R^1$, X and S are as defined in claim 13) and pharmaceutically acceptable salts and esters thereof.

16. A method as claimed in any one of claims 14, 15 or 13, wherein the acyl group represented by $R^1CO$— is selected from the acetyl, propionyl, pivaloyo, benzoyl, 2-methoxycarbonylbenzoyl, 1-naphthoyl, 2-naphthoyl, phenylacetyl, benzyloxycarbonyl, phenylalanyl, N-(benzyloxycarbonyl)phenylalanyl, alpha-(benzyloxycarbonylamino)phenylacetyl, N-(4-phenylbutyryl)-phenylalanyl, 2-hydroxy-3-phenylpropionyl, N-(benzyloxycarbonyl)-tyrosyl, N-(2-nitrophenylthio)-phenylalanyl, N-(3-nitro-2-pyridylthio)phenylalanyl, 2-benzyloxycarbonylamino-3-(1-naphthoyl)propionyl, 2-benzyloxycarbonylamino-3-(2-naphthoyl)propionyl, nicotinyl, 2-pyridinecarbonyl, N-benzyloxycarbonyl-3-(3-quinolyl)-L-alanyl and N-benzyloxycarbonyl-3-(8-quinolyl)-L-alanyl groups, and the groups having the formulae:

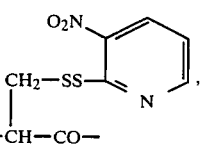

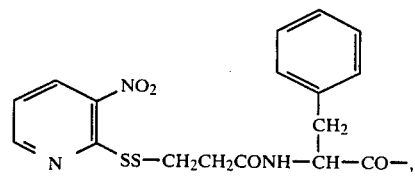

-continued

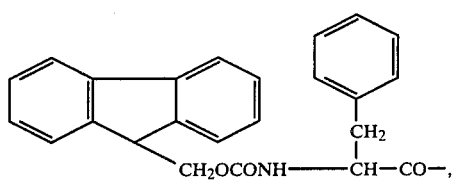

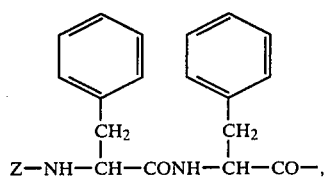

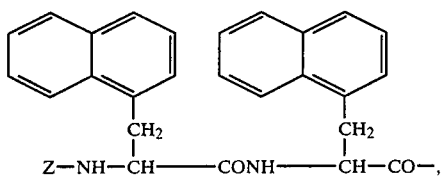

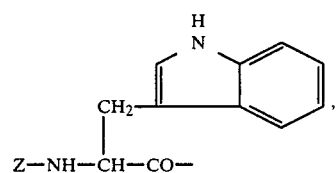

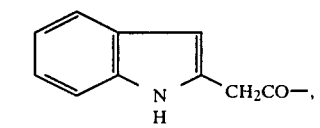

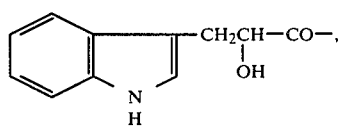

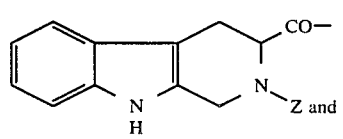

-continued

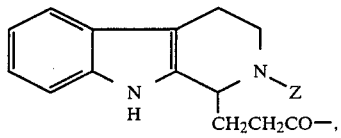

in which Boc represents the t-butoxycarbonyl group and Z represents the benzyloxycarbonyl group.

17. A method as claimed in any one of claims 14, 15 or 13, wherein the group represented by X is selected from the formyl, hydroxymethyl, formylmethyl, 2-formyl-1-hydroxyethyl, 1,2-dihydroxyethyl, 1,3-dihydroxypropyl, 2-hydroxy-1-mercaptoethyl, phosphono, hydroxo(2-hydroxyethyl)oxophosphorio and (formylmethyl)hydroxooxophosphorio groups and groups of formulae

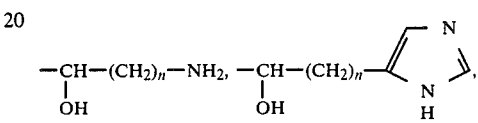

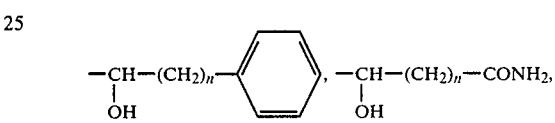

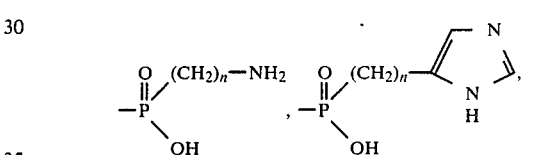

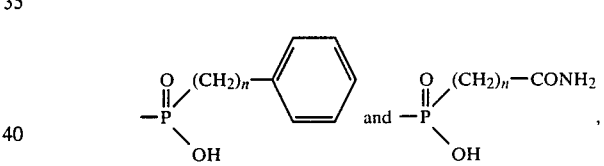

in which n represents an integer from 2 to 8.

18. A method as claimed in claim 13, wherein said renin inhibitor is selected from:

N-(4-phenylbutyryl)-L-phenylalanyl-L-histidyl-L-leucinal,
N-[3-(3-nitro-2-pyridyldithio)propionyl]-L-phenylalanyl-L-histidyl-L-leucinal,
N-benzyloxycarbonyl-3-(1-naphthyl)-L-alanyl-L-histidyl-L-leucinal,
N-benzyloxycarbonyl-L-phenylalanyl-l-histidyl-L-leucinol,
N-[3-(3-nitro-2-pyridyldithio)propionyl]-L-phenylalanyl-L-histidyl-L-leucinol,
N-benzyloxycarbonyl-3-(1-naphthyl)-L-alanyl-L-histidyl-L-leucinol,
and pharmaceutically acceptable salts and esters thereof.

* * * * *